United States Patent [19]

Aloup et al.

[11] Patent Number: 5,777,114

[45] Date of Patent: Jul. 7, 1998

[54] SPIRO|HETEROCYCLE-IMIDAZO|1,2-A| INDENO|1,2-E|PYRAZINE|-4'-ONES, PREPARATION THEREOF AND DRUGS CONTAINING SAME

[75] Inventors: Jean-Claude Aloup, Villeneuve-le-Roi; François Audiau, Charenton-le-Pont; Michel Barreau, Montgeron; Dominique Damour, Orly; Arielle Genevois-Borella, Thiais; Patrick Jimonet, Villepreux; Serge Mignani, Châtenay-Malabry; Yves Ribeill, Villemoisson-sur-Orge, all of France

[73] Assignee: Rhône-Poulenc Rorer S.A., Antony Cedex, France

[21] Appl. No.: 836,410

[22] PCT Filed: Oct. 30, 1995

[86] PCT No.: PCT/FR95/01430

§ 371 Date: Jun. 30, 1997

§ 102(e) Date: Jun. 30, 1997

[87] PCT Pub. No.: WO96/14318

PCT Pub. Date: May 17, 1996

[30] Foreign Application Priority Data

Nov. 2, 1994 [FR] France .................. 94 13060

[51] Int. Cl.⁶ .................. C07D 487/20; C07D 471/20; C07D 487/241; C07D 471/235
[52] U.S. Cl. .................. 544/230; 544/295; 514/215; 514/228.5; 514/269
[58] Field of Search .................. 544/230; 514/250, 514/215, 228.5, 269; 540/576, 597

[56] References Cited

U.S. PATENT DOCUMENTS

| | | | |
|---|---|---|---|
| 4,354,027 | 10/1982 | Loev et al. | 544/346 |
| 5,182,279 | 1/1993 | Jorgensen et al. | 514/250 |
| 5,677,306 | 10/1997 | Aloup et al. | 514/250 |

FOREIGN PATENT DOCUMENTS

| | | |
|---|---|---|
| A-2696466 | 4/1994 | France . |
| WO-A-95/02601 | 1/1995 | WIPO . |

OTHER PUBLICATIONS

English language Derwent Abstract of FR-A-2696466.

*Primary Examiner*—Johann Richter
*Assistant Examiner*—Sabiha N. Qazi

*Attorney, Agent, or Firm*—Finnegan, Henderson, Farabow, Garrett & Dunner, L.L.P.

[57] ABSTRACT

Compounds of formula (I):

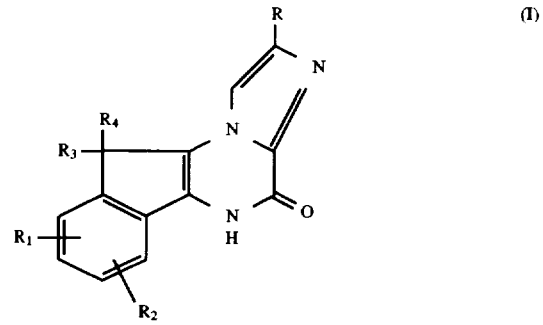

(I)

wherein $R_3$ and $R_4$, taken together with the carbon atom to which they are attached, form (a) a 2- or 3-pyrrolidine ring, a 2- or 4-piperidine ring or a 2-azacycloheptane ring, said rings being optionally substituted at the nitrogen atom by an alkyl, —CHO, —COOR$_{11}$, —CO—alk—COOR$_6$, —CO—alk—NR$_6$R$_{12}$, —CO—alk—CONR$_6$R$_8$, —CO—COOR$_6$, —CO—CH$_2$—O—CH$_2$—COOR$_6$, —CO—CH$_2$—S—CH$_2$—COOR$_6$, —CO—CH=CH—COOR$_6$, CO—alk, —CO—Ar", —CO—alk—Ar", —CO—NH—Ar", —CO—NH—alk—Ar", —CO—Het, —CO—alk—Het, —CO—NH—Het, —CO—NH—alk—Het, —CO—NH$_2$, —CO—NH—alk, —CO—N(alk)alk', —CS—NH$_2$, —CS—NH—alk, —CS—NH—Ar", —CS—NH—Het, —alk—Het, —alk—NR$_6$R$_8$, —alk—COOR$_6$, —alk—CO—NR$_6$R$_8$, —alk—Ar", —SO$_2$—alk or —SO$_2$—Ar radical, or a —CO-cycloalkyl radical where the cycloalkyl is optionally 2-substituted by a carboxyl radical; or (b) a 2-pyrrolidin-5-one ring. The compounds of formula (I) have useful pharmacological properties and are α-amino-3-hydroxy-5-methyl-4-isoxazolepropionic acid (AMPA) receptor antagonists, said receptor also being known as the quisqualate receptor. Furthermore, the compounds of formula (I) are non-competitive N-methyl-D-aspartate (NMDA) receptor antagonists, and especially NMDA receptor glycine modulation site ligands.

23 Claims, No Drawings

SPIRO|HETEROCYCLE-IMIDAZO|1,2-A| INDENO|1,2-E|PYRAZINE|-4'-ONES, PREPARATION THEREOF AND DRUGS CONTAINING SAME

The present invention relates to compounds of formula:

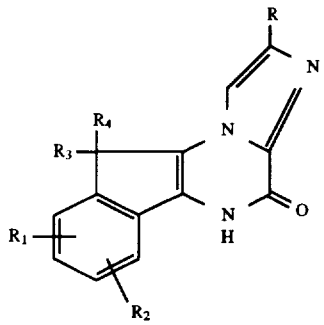

to their salts, to their preparation and to the medicinal products containing them.

In formula (I)

R represents a hydrogen atom or a carboxyl, alkoxycarbonyl or carboxamido radical, $R_1$ and $R_2$, which may be identical or different, represent hydrogen or halogen atoms or alkyl, alkoxy, amino, —N=CH—N(alk)alk', nitro, cyano, phenyl, imidazolyl, $SO_3H$, hydroxyl, polyfluoroalkoxy, carboxyl, alkoxycarbonyl, —NH—CO—$NR_5R_6$, —N(alk)—CO—$NR_5R_6$, —N(alk—Ar)—CO—$NR_5R_6$, —NH—CS—$NR_5R_6$, —N(alk)—CS—$NR_5R_6$, —NH—CO—$R_5$, —NH—CS—$R_7$, —NH—C(=$NR_9$)—$NR_8R_6$, —N(alk)—C(=$NR_9$)—$NR_8R_6$, —CO—$NR_8R_6$, —NH—$SO_2$—$NR_8R_6$, —N(alk)—$SO_2$—$NR_8R_6$, —NH—$SO_2$—$CF_3$, —NH—$SO_2$—alk, —NH—$SO_2$—Ar, —$NR_8R_{10}$, —$S(O)_m$—alk—Ar or —$SO_2$—$NR_8R_6$ radicals or a 2-oxo-1-imidazolidinyl radical in which the 3-position is optionally substituted with an alkyl radical, or a 2-oxoperhydro-1-pyrimidinyl radical in which the 3-position is optionally substituted with an alkyl radical, $R_3$ and $R_4$, together with the carbon atom to which they are attached, form (a) a 2- or 3-pyrrolidine ring, a 2- or 4-piperidine ring or a 2-azacycloheptane ring, these rings optionally being substituted on the nitrogen with an alkyl, —CHO, —$COOR_{11}$, —CO—alk—$COOR_6$, —CO—alk—$NR_6R_{12}$, —CO—alk—$CONR_6R_8$, —CO—$COOR_6$, —CO—$CH_2$—O—$CH_2$—$COOR_6$, —CO—$CH_2$—S—$CH_2$—$COOR_6$, —CO—CH=CH—$COOR_6$, CO—alk, —CO—Ar", —CO—alk—Ar", —CO—NH—Ar", —CO—NH—alk—Ar", —CO—Het, —CO—alk—Het, —CO—NH—Het, —CO—NH—alk—Het, —CO—$NH_2$, —CO—NH—alk, —CO—N(alk)alk', —CS—$NH_2$, —CS—NH—alk, —CS—NH—Ar", —CS—NH—Het, —alk—Het, —alk—$NR_6R_8$, —alk—$COOR_6$, —alk—CO—$NR_6R_8$, —alk—Ar", —$SO_2$—alk or —$SO_2$—Ar radical or a —CO—cycloalkyl radical in which the cycloalkyl is optionally substituted in the 2-position with a carboxyl radical, or (b) a 2-pyrrolidin-5-one ring, $R_5$ represents a hydrogen atom or an alkyl (1–9C in a straight or branched chain), —alk—$COOR_8$, —alk—Het or —alk—$NR_6R_8$ radical, a phenylalkyl radical in which the phenyl ring is optionally substituted with one or more substituents chosen from halogen atoms and alkyl, alkoxy, nitro, amino, hydroxyl, —alk—$NH_2$, carboxyl, alkoxycarbonyl, cyano and —alk—$COOR_8$ radicals, a phenyl radical which is optionally substituted with one or more substituents chosen from halogen atoms and alkyl, alkoxy, nitro, amino, hydroxyl, —alk—$NH_2$, carboxyl, alkoxycarbonyl, cyano and —alk—$COOR_8$ radicals, or a —Het radical, $R_6$ represents a hydrogen atom or an alkyl radical, $R_7$ represents an alkyl or phenyl radical, $R_8$ represents a hydrogen atom or an alkyl radical, $R_9$ represents a hydrogen atom or an alkyl radical, $R_{10}$ represents an alkyl, Het or alkoxycarbonyl radical, $R_{11}$ represents an alkyl or phenylalkyl radical, $R_{12}$ represents a hydrogen atom or an alkyl or —CO—NH—alk radical, alk represents an alkyl or alkylene radical, alk' represents an alkyl radical, m is equal to 0, 1 or 2, Ar represents a phenyl radical, Ar" is a phenyl radical or a phenyl radical substituted with one or more substituents chosen from halogen atoms and alkyl, alkoxy, nitro, amino, hydroxyl, cyano, —alk—$NH_2$, $COOR_6$ and —alk—$COOR_6$ radicals, Het represents (a) a saturated or unsaturated mono- or polycyclic heterocycle containing 1 to 9 carbon atoms and one or more heteroatoms (O, S or N) which is optionally substituted with one or more alkyl, phenyl, carboxyl or phenylalkyl radicals, or (b) a phthalimido radical.

Except where otherwise mentioned, in the preceding definitions and in those which follow, the alkyl, alkylene and alkoxy radicals and portions contain 1 to 6 carbon atoms and are in a straight or branched chain, the cycloalkyl radicals contain 3 to 6 carbon atoms and the halogen atoms are chosen from fluorine, chlorine, bromine and iodine.

Het is preferably chosen from a pyrrolyl ring optionally substituted with one or more alkyl, phenyl, carboxyl or phenylalkyl radicals, a pyridyl ring optionally substituted with one or more alkyl, phenyl, carboxyl or phenylalkyl radicals, a pyrimidinyl ring optionally substituted with one or more alkyl, phenyl, carboxyl or phenylalkyl radicals, an imidazolyl ring optionally substituted with one or more alkyl, phenyl, carboxyl or phenylalkyl radicals, a thiazolyl ring optionally substituted with one or more alkyl, phenyl, carboxyl or phenylalkyl radicals, an oxazolinyl ring optionally substituted with one or more alkyl, phenyl, carboxyl or phenylalkyl radicals, a thiazolinyl ring optionally substituted with one or more alkyl, phenyl, carboxyl or phenylalkyl radicals, a pyrazinyl ring optionally substituted with one or more alkyl, phenyl, carboxyl or phenylalkyl radicals, a tetrazolyl ring optionally substituted with one or more alkyl, phenyl, carboxyl or phenylalkyl radicals, or a triazolyl ring optionally substituted with one or more alkyl, phenyl, carboxyl or phenylalkyl radicals. The preferred substituents are the methyl, phenyl, carboxyl and benzyl radicals.

The enantiomers and diastereoisomers of the compounds of formula (I) for which $R_3$ and $R_4$, together with the carbon atom to which they are attached, form a 2- or 3-pyrrolidine ring, a 2-pyrrolidin-5-one ring, a 2-piperidine ring or a 2-azacycloheptane ring also form part of the invention, as well as the cis and trans isomers of the compounds of formula (I) containing a radical —CO—CH=CH—$COOR_6$.

The compounds of formula (I) for which $R_3$ and $R_4$, together with the carbon atom to which they are attached, form a 2-pyrrolidine ring, a 2-piperidine ring or a 2-azacycloheptane ring may be prepared by the action of a derivative of formula:

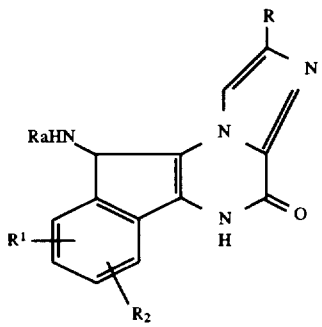
(II)

in which Ra represents a protecting group for the amine function such as a tert-butoxycarbonyl radical, and R, $R_1$ and $R_2$ have the same meanings as in formula (I), on a derivative of formula:

Hal—(CH$_2$)$_p$—Hal' (III)

in which Hal and Hal', which may be identical or different, are halogen atoms (preferably chlorine and bromine) and p is equal to 3, 4 or 5, followed by deprotection of the NH.

The condensation is carried out in an inert solvent such as dimethyl sulphoxide, in the presence of an alkali metal hydride (for example sodium hydride), at a temperature in the region of 20° C.

The NH is deprotected by any method known to those skilled in the art, such as those described by W. Greene et al., "Protecting Groups in Organic Synthesis", second edition, 1991, John Wiley & Sons. In particular, when the protecting group is a tert-butoxycarbonyl radical, the process is performed using trifluoroacetic acid at a temperature in the region of 20° C.

The derivatives of formula (II) may be obtained by protection of the amine function in the corresponding derivatives for which Ra represents a hydrogen atom.

This protection is carried out by all the known processes for protecting an amine function, such as those described by W. Greene et al., "Protecting Groups in Organic Synthesis", second edition, 1991, John Wiley & Sons. In the case where Ra represents a tert-butoxycarbonyl radical, di-tert-butyl carbonate is preferably reacted, in an inert solvent such as dimethylformamide, at a temperature in the region of 20° C.

The derivatives of formula (II) for which Ra represents a hydrogen atom may be obtained by hydrolysis of the corresponding compounds of formula (II) for which Ra represents an alkylcarbonyl radical, followed, for the compounds for which R represents an alkoxycarbonyl radical, by esterification of the corresponding acid.

This hydrolysis is generally carried out using an acid such as hydrochloric acid, in aqueous medium, at the boiling point of the reaction medium. The esterification is carried out using an alcohol (C1–C6 in a straight or branched chain), in acidic medium (hydrochloric or sulphuric acid for example), at the boiling point of the reaction medium.

The derivatives of formula (II) for which Ra represents an alkylcarbonyl radical may be obtained by reduction of a derivative of formula:

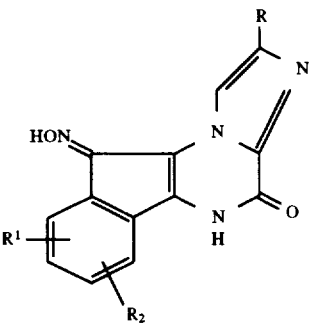
(IV)

in which R, $R_1$ and $R_2$ have the same meanings as in formula (I), in the presence of an acid alk—COOH, followed by the action of the acid anhydride (alkCO)$_2$O in which alk represents an alkyl radical.

The reduction is generally carried out at a temperature of between 50° and 100° C. Zinc is preferably used as reducing agent. The reaction with the anhydride is preferably carried out at a temperature in the region of 20° C.

The derivatives of formula (IV) may be obtained by the action of an alkyl nitrite on a derivative of formula:

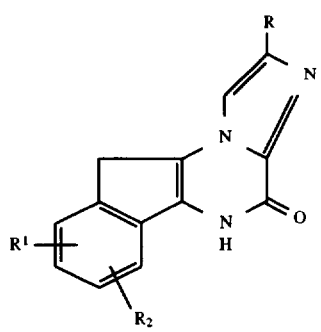
(V)

in which R, $R_1$ and $R_2$ have the same meanings as in formula (I).

This reaction is preferably carried out in an inert solvent such as dimethyl sulphoxide, in the presence of an alkali metal hydride such as sodium hydride, at a temperature in the region of 20° C. Isoamyl nitrite is preferably used.

The derivatives of formula (V) for which R represents a hydrogen atom may be obtained by dealkylation and desalification of a derivative of formula:

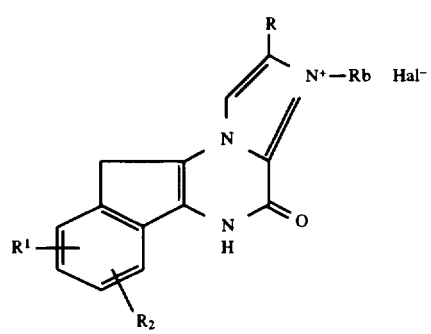
(VI)

in which R represents a hydrogen atom, $R_1$ and $R_2$ have the same meanings as in formula (I), Rb represents an alkyl radical and Hal represents a halogen atom (preferably bromine).

This reaction is preferably carried out in the presence of imidazole, at a temperature of between 100° and 200° C.

The derivatives of formula (VI) may be obtained by the action of a derivative of formula:

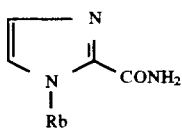

in which Rb has the same meanings as in formula (VI), on a haloindanone of formula:

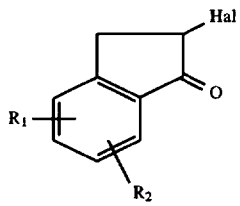

in which $R_1$ and $R_2$ have the same meanings as in formula (I) and Hal represents a halogen atom.

This reaction is generally carried out in an inert solvent such as dimethylformamide, at a temperature of between 50° and 150° C. and preferably at 115° C.

The derivatives of formula (VII) may be obtained by application or adaptation of the method described by D. D. Davey, J. Org. Chem., 52, 4379 (1987).

The derivatives of formula (VIII) may be obtained by application or adaptation of the method described by Olivier et al., Bull. Soc. Chim. France, 3092 (1973) and in patent DE 2,640,358.

The derivatives of formula (V) for which R represents an alkoxycarbonyl radical, with the exception of tert-butoxycarbonyl, may be obtained by cyclization of a derivative of formula:

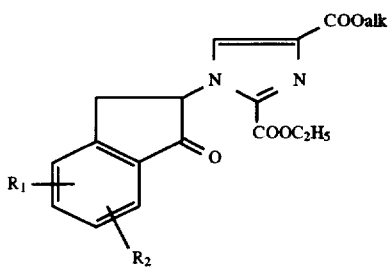

in which $R_1$ and $R_2$ have the same meanings as in formula (I) and alk represents an alkyl radical except tert-butyl.

This cyclization is generally carried out in acetic acid, in the presence of ammonium acetate, at the boiling point of the reaction medium.

The derivatives of formula (IX) may be obtained by the action of an ethyl 4-alkoxycarbonyl-2-imidazolecarboxylate on a derivative of formula (VIII) in which $R_1$ and $R_2$ have the same meanings as in formula (I) and Hal represents a halogen atom.

This reaction is generally carried out in an inert solvent such as an alcohol (for example methanol or ethanol), a ketone (for example acetone), an aromatic hydrocarbon (for example toluene) or dimethylformamide, or in the absence of solvent, optionally in the presence of an organic base such as sodium hydride or potassium carbonate, at a temperature between 20° C. and the boiling point of the reaction medium or the melting point of the reaction medium.

The ethyl 4-alkoxycarbonyl-2-imidazolecarboxylates may be obtained by application or adaptation of the method described by P. S. Branco et al., Tetrahedron, 48 (30), 6335 (1992).

The derivatives of formula (V) for which R represents a tert-butoxycarbonyl radical may be obtained by the action of isobutene on a corresponding derivative of formula (V) for which R represents a carboxyl radical.

This reaction is generally carried out in an inert solvent such as dichloromethane or dioxane, in the presence of concentrated sulphuric acid, at a temperature between 20° C. and the boiling point of the reaction medium.

The derivatives of formula (V) for which R represents a carboxyl radical may be obtained by cyclization of a derivative of formula (IX) for which alk represents a tert-butyl radical.

This cyclization is generally carried out in acetic acid, in the presence of ammonium acetate, at the boiling point of the reaction medium.

The derivatives of formula (V) for which R represents a carboxamide radical may be obtained by cyclization of a derivative of formula:

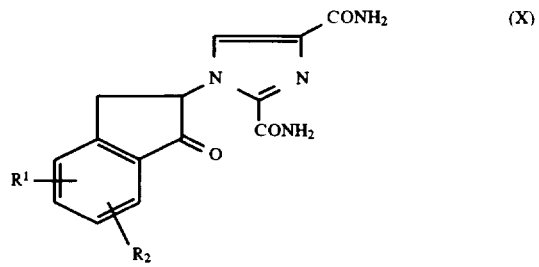

in which $R_1$ and $R_2$ have the same meanings as in formula (I).

This cyclization is generally carried out using an acid such as hydrochloric acid or acetic acid, in aqueous solution, at a temperature of between 20° C. and the boiling point of the reaction medium.

The derivatives of formula (X) may be obtained by the action of ammonia on a corresponding derivative of formula (IX).

This reaction is generally carried out in an inert solvent such as an alcohol, optionally in an autoclave, at a temperature of between −30° C. and 100° C.

The compounds of formula (I) for which $R_3$ and $R_4$, together with the carbon atom to which they are attached, form a 3-pyrrolidine ring may be prepared by condensation of N-n-butoxymethyl-N-trimethylsilylmethylbenzylamine with a derivative of formula:

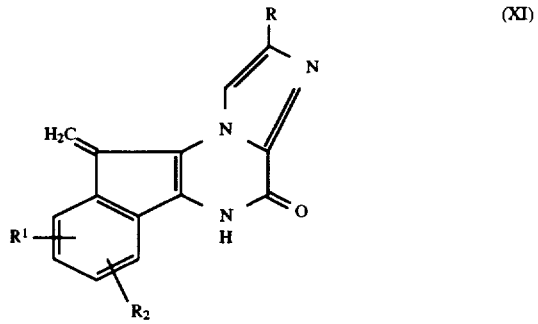

in which R, $R_1$ and $R_2$ have the same meanings as in formula (I), followed by debenzylation of the NH.

The condensation is carried out in an inert solvent such as dimethylformamide, in the presence of a catalytic amount of trifluoroacetic acid, at a temperature of between 15° and 70° C. The debenzylation is generally carried out using hydrogen, in an inert solvent (for example dimethylformamide or acetic acid), in the presence of a hydrogenation catalyst such as palladium-on-charcoal, palladium hydroxide or palladium, at a hydrogen pressure of between 1 and 20 bar, and at a temperature of between 20° and 50° C.

N-n-Butoxymethyl-N-trimethylsilylmethylbenzylamine may be obtained by the method described by Y. Terao et al., Chem. Pharm. Bull., 33, 2762 (1985).

The derivatives of formula (XI) may be obtained by application or adaptation of the method described in the examples.

The compounds of formula (I) for which $R_3$ and $R_4$, together with the nitrogen atom to which they are attached, form a 4-piperidine ring may be prepared by the action of N,N-bis(2-chloroethyl)-p-toluenesulphonamide on a derivative of formula (V) in which R, $R_1$ and $R_2$ have the same meanings as in formula (I), followed by hydrolysis of the sulphonamide function.

This reaction is preferably carried out in an inert solvent such as dimethyl sulphoxide, in the presence of an alkali metal hydride (for example sodium hydride), at a temperature in the region of 20° C. Hydrolysis of the sulphonamide function is preferably carried out in an acid such as hydrobromic acid, at the boiling point of the reaction medium.

The compounds of formula (I) for which $R_3$ and $R_4$, together with the carbon atom to which they are attached, form a 2-pyrrolidin-5-one ring may be prepared by the action of a derivative of formula (II) in which Ra represents an acetyl radical and R, $R_1$ and $R_2$ have the same meanings as in formula (I), on methyl 3-bromopropionate.

This reaction is generally carried out in dimethyl sulphoxide, in the presence of sodium hydride, at a temperature of between 20° and 30° C.

The derivatives of formula (II) in which Ra represents an acetyl radical and R, $R_1$ and $R_2$ have the same meanings as in formula (I) may be prepared by application or adaptation of the method described in patent FR 2,707,643.

The compounds of formula (I) for which $R_3$ and $R_4$, together with the carbon atom to which they are attached, form a 2- or 3-pyrrolidine ring, a 2- or 4-piperidine ring or a 2-azacycloheptane ring, in which the nitrogen atom is substituted with an alkyl (1C) radical, may be prepared by the action of formaldehyde and formic acid on a corresponding compound of formula (I) for which $R_3$ and $R_4$, together with the carbon atom to which they are attached, form a 2- or 3-pyrrolidine ring, a 2- or 4-piperidine ring or a 2-azacycloheptane ring.

This reaction is carried out at a temperature of between 20° and 35° C.

The compounds of formula (I) for which $R_3$ and $R_4$, together with the carbon atom to which they are attached, form a 2- or 3-pyrrolidine ring, a 2- or 4-piperidine ring or a 2-azacycloheptane ring in which the nitrogen atom is substituted with an alkyl (2–6C) radical, may be prepared by the action of an acid alk—COOH in which alk represents an alkyl (1–5C) radical, on a corresponding compound of formula (I) for which $R_3$ and $R_4$, together with the carbon atom to which they are attached, form a 2- or 3-pyrrolidine ring, a 2- or 4-piperidine ring or a 2-azacycloheptane ring, in the presence of sodium borohydride.

This reaction is carried out in the presence of an excess of the acid alk—COOH which serves as solvent, at a temperature in the region of 45° C.

The compounds of formula (I) for which $R_3$ and $R_4$, together with the carbon atom to which they are attached, form a 2- or 3-pyrrolidine ring, a 2- or 4-piperidine ring or a 2-azacycloheptane ring in which the nitrogen atom is substituted with a radical —CO—alk—$NR_6R_{12}$ in which $R_6$ and $R_{12}$ each represent a hydrogen atom, may be prepared by the action of a corresponding compound of formula (I) for which $R_3$ and $R_4$, together with the carbon atom to which they are attached, form a 2- or 3-pyrrolidine ring, a 2- or 4-piperidine ring or a 2-azacycloheptane ring, on a derivative of formula:

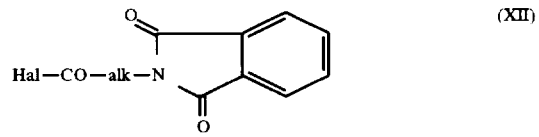

in which Hal represents a halogen atom and alk represents an alkyl radical, followed by deprotection of the $NH_2$.

This reaction is generally carried out in an inert solvent such as dimethylformamide, in the presence of an acid acceptor such as a nitrogen-containing organic base (for example pyridine or a trialkylamine such as triethylamine), at a temperature between 0° C. and the boiling point of the reaction medium. The deprotection is carried out in a lower aliphatic alcohol (for example ethanol), in the presence of hydrazine, at the boiling point of the reaction medium.

The derivatives of formula (XII) may be obtained by application or adaptation of the method described by K. Balenovic et al., J. Org. Chem., 17, 1149 (1952).

The compounds of formula (I) for which $R_3$ and $R_4$, together with the carbon atom to which they are attached, form a 2- or 3-pyrrolidine ring, a 2- or 4-piperidine ring or a 2-azacycloheptane ring in which the nitrogen atom is substituted with an alkyl (2–6C), —$COOR_{11}$, —alk—Het, —alk—$NR_6R_8$, —alk—$COOR_6$, —alk—Ar", —CO—alk, —CO—alk—$COOR_6$, —CO—alk—$NR_6R_{12}$ or —CO—$COOR_6$ radical, or a radical —CO-cycloalkyl in which the cycloalkyl is optionally substituted in the 2-position with a carboxyl, —CO—Ar", —CO—alk—Ar", —CO—Het, —CO—alk—Het, —CO—N(alk)alk', —$SO_2$—alk or —$SO_2$—Ar radical, may be prepared by the action of a corresponding compound of formula (I) for which $R_3$ and $R_4$, together with the carbon atom to which they are attached, form a 2- or 3-pyrrolidine ring, a 2- or 4-piperidine ring or a 2-azacycloheptane ring, on a halide Hal—Rc in which Hal represents a halogen atom and Rc represents an alkyl (2–6C), —$COOR_{11}$, —alk—Het, —alk—$NR_6R_8$, —alk—$COOR_6$, —alk—Ar", —CO—alk, —CO—alk—$COOR_6$, —CO—alk—$NR_6R_{12}$ or —CO—$COOR_6$ radical or a radical —CO-cycloalkyl(3–6C) in which the cycloalkyl is optionally substituted in the 2-position with a carboxyl, —CO—Ar", —CO—alk—Ar", —CO—Het, —CO—alk—Het, —CO—N(alk)alk', —$SO_2$—alk or —$SO_2$—Ar radical, alk, alk', Het, $R_6$, $R_8$, $R_{11}$, $R_{12}$, Ar and Ar" having the same meanings as in formula (I).

This reaction is generally carried out in an inert solvent such as dimethylformamide, in the presence of an acid acceptor such as an alkali metal carbonate (for example sodium or potassium carbonate), a trialkylamine (for example triethylamine) or pyridine, at a temperature of between 0° C. and the boiling point of the reaction medium.

The halides Hal—Rc are commercially available or may be prepared according to the following methods:

those for which Rc represents a radical —alk—$NR_6R_8$ may be obtained by the action of the amine $HNR_6R_8$, in which $R_6$ and $R_8$ have the same meanings as in formula (I), on a halide Hal—alk—Hal in which Hal represents a halogen atom and alk represents an alkyl radical, in an inert solvent such as dimethylformamide, in the presence of an acid acceptor such as a nitrogen-containing base, at a temperature of between 0° and 25° C., those for which Rc represents a radical —alk—$COOR_6$ may be obtained by the action of a derivative Hal— alk—Hal, in which Hal represents a halogen atom and alk represents an alkyl radical, on an alkali metal cyanide (sodium or potassium cyanide), in a water/alcohol mixture, at a temperature of between 0° C. and the boiling point of the reaction medium, followed by the action of a strong acid such as hydrochloric acid, optionally in the presence of a lower aliphatic alcohol, at a temperature of between 0° C. and the boiling point of the reaction medium, those for which Rc represents a radical —CO—alk, —CO—alk—COOR$_6$, —CO—alk—NR$_6$R$_{12}$, —CO—COOR$_6$, —CO-cycloalkyl, —CO—Ar", —CO—alk—Ar", —CO—Het or —CO—alk—Het may be obtained by heating a corresponding acid HO—Rc, in which Rc is defined as above, and a halogenation reagent such as thionyl chloride, thionyl bromide or a phosphorus halide (for example PCl$_5$ or POCl$_3$), in an inert solvent such as a chlorinated solvent (for example 1,2-dichloroethane), at a temperature of between 20° C. and the boiling point of the reaction medium. The corresponding acids are commercially available or the acids HOOC—alk—NR$_6$R$_{12}$ may be obtained by the action of a halide alkOOC—alk—Hal, in which Hal represents a halogen atom and alk an alkyl radical, on an amine HNR$_6$R$_{12}$ in which R$_6$ and R$_{12}$ have the same meanings as in formula (I), in the presence of an alkali metal carbonate or a trialkylamine, at a temperature of between 20° C. and the boiling point of the reaction medium, followed by hydrolysis in basic medium (sodium hydroxide/alcohol), at a temperature of between 0° and 60° C., and acidification using an acid (for example HCl), at a temperature of between 20° and 60° C. The acids HOOC—Het, HOOC—alk—Het, HOOC—Ar" and HOOC—alk—Ar" may be obtained from the heterocycle and the corresponding optionally substituted benzene by application or adaptation of the methods described by L. Estel et al., J. Heterocyclic Chem., 26, 105 (1989); N. S. Narasimhan et al., Synthesis, 957 (1983); A. Turck et al., Synthesis, 881 (1988), A. J. Clarke et al., Tetrahedron Lett., 27, 2373 (1974); A. R. Katritzky et al., Org. Perp. Procedure Int., 20 (6), 585 (1988); N. Furukawa et al., Tetrahedron Lett., 28 (47), 5845 (1987); H. W. Gschwend et al., Organic Reactions, 26, 1 (1979) and V. Snieckus, Chem. Rev., 90, 879 (1990). Preferably, the corresponding organometallic derivative of the heterocycle or of the optionally substituted benzene (for example the organolithium or organomagnesium derivative) is prepared and is reacted either with CO$_2$ or with a derivative Hal—alk—COOalk, in which Hal represents a halogen atom and alk represents an alkyl radical, followed by a hydrolysis reaction which is generally carried out using a base such as an alkali metal hydroxide (for example sodium hydroxide or potassium hydroxide) in a water/lower aliphatic alcohol mixture, at a temperature of between 20° and 80° C. The derivatives Hal—alk—COOalk are commercially available or may be obtained by the action of Hal—alk—Hal, in which Hal represents a halogen atom and alk represents an alkyl radical, on an alkali metal cyanide such as sodium or potassium cyanide, in a water/lower aliphatic alcohol mixture, at a temperature of between 0° C. and the boiling point of the reaction medium, followed by the action of an acid such as hydrochloric acid, in the presence of an alcohol, at a temperature of between 0° C. and the boiling point of the reaction medium. The acids HOOC—alk—COOR$_6$ may be obtained from the corresponding diacids by application or adaptation of the method described by D. Rehn et al., J. Chem. Research (s), 119 (1977), those for which Rc represents a radical —alk—Het or —alk—Ar" may be obtained from the corresponding alcohols HO—Rc, in which Rc is defined as above, by application or adaptation of the methods described by R. C. Larock, "Comprehensive Organic Transformations", ed. VCH, page 353 (1989). The corresponding alcohols HO—alk—Het and HO—alk—Ar" are commercially available or may be obtained from the corresponding organometallic derivatives by application or adaptation of the methods described by L. Estel et al., J. Heterocyclic Chem., 26, 105 (1989); N. S. Narasimhan et al., Synthesis, 957 (1983); and Tetrahedron Lett., 22, (29) 2797 (1981); H. W. Gschwend et al., Organic Reactions, 26, 1 (1979), V. Snieckus, Chem. Rev., 90, 879 (1990) and F. Marchais et al., J. Heterocyclic Chem, 25, 81 (1988). Preferably the organolithium or organomagnesium derivative of the heterocycle or of the optionally substituted benzene is reacted with formaldehyde, an aldehyde, a ketone, an epoxide or Hal—alk—OP, where P is a protecting group (for example methyl ether, tetrahydropyranyl ether, benzyl ether or triethylsilyl ether), followed by liberation of the alcohol function by application or adaptation of the methods described by W. Greene et al., "Protecting Groups in Organic Synthesis", second edition, 1991, John Wiley & Sons. The corresponding alcohols HO—alk—Het and HO—alk—Ar" may also be obtained by reduction of the corresponding carboxylic acids or esters using lithium aluminium hydride, in an inert solvent such as tetrahydrofuran or diethyl ether, at the boiling point of the reaction medium. The alcohols HO—alk(2–6C)—Het may also be obtained by application or adaptation of the method described by J. T. Meyer et al., Helv. Chem. Acta, 65, 1868 (1982) starting with the derivatives Hal—alk(1-5C)—Het in which Hal represents a halogen atom and alk represents an alkyl radical, which derivatives are themselves obtained by the action of a halogenating agent (halogenated phosphorus derivative or thionyl chloride) on a corresponding derivative HO—alk (1–5C)—Het, optionally in an inert solvent such as dichloromethane, at a temperature of between 20° and 40° C., those for which Rc represents a radical —SO$_2$—alk or —SO$_2$—Ar may be prepared by halogenation of the corresponding sulphonic acids using a halogenated phosphorus derivative or thionyl chloride, in an inert solvent such as dichloromethane, at a temperature of between 20° and 40° C., those for which Rc represents a radical —COOR$_{11}$ may be obtained by application or adaptation of the methods described in Houben Weyl, volume 8, page 102 (1952).

The compounds of formula (I) for which R$_3$ and R$_4$, together with the carbon atom to which they are attached, form a 2- or 3-pyrrolidine ring, a 2- or 4-piperidine ring or a 2-azacycloheptane ring in which the nitrogen atom is substituted with a radical —CO—alk—CONR$_6$R$_8$ or —alk—CO—NR$_6$R$_8$, may be prepared by the action of a corresponding compound of formula (I) for which R$_3$ and R$_4$, together with the carbon atom to which they are attached, form a 2- or 3-pyrrolidine ring, a 2- or 4-piperidine ring or a 2-azacycloheptane ring in which the nitrogen atom is substituted with a radical —CO—alk—COOR$_6$ or —alk—COOR$_6$, on an amine HNR$_6$R$_8$ in which R$_6$ and R$_8$ have the same meanings as in formula (I).

11

When the acid is used, the process is performed in the presence of a coupling agent used in peptide chemistry, such as a carbodiimide (for example N,N'-dicyclohexylcarbodiimide) or N,N'-carbonyldiimidazole, in an inert solvent such as an ether (for example tetrahydrofuran or dioxane), an amide (dimethylformamide) or a chlorinated solvent (for example methylene chloride, 1,2-dichloroethane or chloroform) at a temperature of between 0° C. and the reflux temperature of the reaction mixture. When an ester is used, the process is then performed in organic medium, optionally in the presence of an acid acceptor such as a nitrogen-containing organic base (for example a trialkylamine, pyridine, 1,8-diazabicyclo|5.4.0|-undec-7-ene or 1,5-diazabicyclo|4.3.0|non-5-ene), in a solvent as mentioned above, or a mixture of these solvents, at a temperature of between 0° C. and the reflux temperature of the reaction mixture, or in a two-phase aqueous-organic medium in the presence of an alkali metal or alkaline-earth metal base (sodium hydroxide or potassium hydroxide) or an alkali metal or alkaline-earth metal carbonate or bicarbonate, at a temperature of between 0° C. and the boiling point of the reaction medium.

The compounds of formula (I) for which $R_3$ and $R_4$, together with the carbon atom to which they are attached, form a 2- or 3-pyrrolidine ring, a 2- or 4-piperidine ring or a 2-azacycloheptane ring in which the nitrogen atom is substituted with a —CHO radical may be prepared by the action of a corresponding compound of formula (I) for which $R_3$ and $R_4$, together with the carbon atom to which they are attached, form a 2- or 3-pyrrolidine ring, a 2- or 4-piperidine ring or a 2-azacycloheptane ring, on $CH_3COOCHO$.

This reaction is preferably carried out in an inert solvent such as formic acid, in the presence of sodium acetate, at a temperature in the region of 20° C.

The compounds of formula (I) for which $R_3$ and $R_4$, together with the carbon atom to which they are attached, form a 2- or 3-pyrrolidine ring, a 2- or 4-piperidine ring or a 2-azacycloheptane ring in which the nitrogen atom is substituted with a radical —CO—Het, —CO—alk—COOR$_6$, —CO—COOR$_6$, —CO—alk—NR$_6$R$_{12}$, —CO—Ar", —CO—alk—Ar", —CO—alk—Het or —CO—alk or a radical —CO-cycloalkyl in which the cycloalkyl is optionally substituted in the 2-position with a carboxyl radical, may also be prepared by the action of a corresponding compound of formula (I) for which $R_3$ and $R_4$, together with the carbon atom to which they are attached, form a 2- or 3-pyrrolidine ring, a 2- or 4-piperidine ring or a 2-azacycloheptane ring, on a derivative HO—Rd in which Rd represents a radical —CO—Het, —CO—alk—COOR$_6$, —CO—COOR$_6$, —CO—alk—NR$_6$R$_{12}$, —CO—Ar", —CO—alk—Ar", —CO—alk—Het or —CO—alk, or a radical —CO-cycloalkyl(3–6C) in which the cycloalkyl is optionally substituted in the 2-position with a carboxyl radical, Het, alk, R$_6$, R$_8$, R$_{12}$, Het and Ar" having the same meanings as in formula (I).

This reaction is generally carried out in an inert solvent such as dimethylformamide, in the presence of hydroxybenzotriazole or 1-(3-dimethylaminopropyl)-3-ethylcarbodiimide and an organic base such as a trialkylamine (for example triethylamine), at a temperature of between 0° and 30° C.

The compounds of formula (I) for which $R_3$ and $R_4$, together with the carbon atom to which they are attached, form a 2- or 3-pyrrolidine ring, a 2- or 4-piperidine ring or a 2-azacycloheptane ring in which the nitrogen atom is substituted with a radical —CO—alk—COOR$_6$ in which alk contains 1 to 3 carbon atoms in a straight chain, a radical —CO—CH$_2$—C(CH$_3$)$_2$—CH$_2$—COOR$_6$, —CO—CH$_2$—CH$_2$—C(CH$_3$)$_2$—COOR$_6$, —CO—CH$_2$—C(CH$_3$)$_2$—COOR$_6$, —CO—CH$_2$—O—CH$_2$—COOR$_6$, —CO—CH$_2$—S—CH$_2$—COOR$_6$ or —CO—CH=CH—COOR$_6$, a radical —CO-cycloalkyl (6C) in which the cycloalkyl is substituted in the 2-position with a carboxyl radical, a radical —CO—Ar" in which Ar" represents a phenyl radical substituted in the 2-position with a carboxyl radical, or a radical —CO—Het in which Het represents a 2- or 4-pyridyl radical substituted in the 3-position with a carboxyl radical or a 3-pyridyl radical substituted in the 4-position with a carboxyl radical and R$_6$ represents a hydrogen atom, may be prepared by the action of an anhydride of formulae:

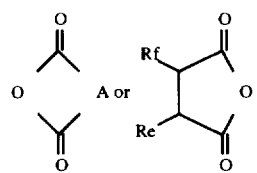

in which A represents an alkyl (1–3C in a straight chain), —CH$_2$—C(CH$_3$)$_2$—CH$_2$—, —CH$_2$—CH$_2$—C(CH$_3$)$_2$—, —CH$_2$—C(CH$_3$)$_2$—, —CH$_2$—O—CH$_2$—, —CH$_2$—S—CH$_2$ or —CH=CH—, Re and Rf form, together with the 2 carbon atoms to which they are attached, a cycloalkyl(6C), phenyl or pyridyl radical, on a corresponding compound of formula (I) for which $R_3$ and $R_4$, together with the carbon atom to which they are attached, form a 2- or 3-pyrrolidine ring, a 2- or 4-piperidine ring or a 2-azacycloheptane ring.

This reaction is generally carried out in an inert solvent such as acetic acid, at a temperature in the region of 20° C., or in the presence of 4-dimethylaminopyridine in dioxane, at the boiling point of the reaction medium.

The compounds of formula (I) for which $R_3$ and $R_4$, together with the carbon atom to which they are attached, form a 2- or 3-pyrrolidine ring, a 2- or 4-piperidine ring or a 2-azacycloheptane ring in which the nitrogen atom is substituted with a radical —CO—NH—alk—Ar", —CO—NH—Het, —CO—NH—alk—Het, —CO—NH—Ar", —CO—NH—alk, —CO—NH$_2$, —CSNH$_2$, —CS—NH—alk, —CS—NH—Ar" or —CS—NH—Het may be prepared by the action of a corresponding compound of formula (I) for which $R_3$ and $R_4$, together with the carbon atom to which they are attached, form a 2- or 3-pyrrolidine ring, a 2- or 4-piperidine ring or a 2-azacycloheptane ring on a derivative of formula Rg=C=N—Rh in which Rg represents an oxygen or sulphur atom and Rh represents a trimethylsilyl, alkyl, Het, —alk—Ar", —alk—Het or Ar" radical, Het, alk and Ar" having the same meanings as in formula (I).

This reaction is preferably carried out in an inert solvent such as dimethylformamide, tetrahydrofuran or dioxane, at a temperature of between 20° C. and the boiling point of the reaction medium, optionally followed by hydrolysis of the silyl derivative previously obtained, using an aqueous solution, at a temperature of between 20° and 50° C.

The derivatives O=C=N—Rh are commercially available or may be obtained by the action of phosgene on the corresponding primary amine H$_2$N—Rh, by adaptation of the methods described by R. L. Shriner et al., Organic Synth., II, 453; G. M. Dyon, Organic Synth., I, 165; R. J. Slocompie et al., J. Am. Chem. Soc., 72, 1888 (1950) and S. Patai, "The chemistry of cyanates and their thio derivatives", Ed. John Wiley and Sons, page 619 (1977). The corresponding primary amines are commercially available, or those for which Rh represents a radical Het or Ar" may be obtained by application or adaptation of the methods described by B. A. Tertov et al., Khim. Geterotsikl. Soedin, II, 1552 (1972) and R. C. Larock, "Comprehensive Organic Transformations", Ed. VCH, page 399, which consists in reacting the organolithium or organomagnesium derivative of the heterocycle or of the optionally substituted benzene with $PhN_3$, in the presence of acetic acid, $NH_2OCH_3$, $(PHO)_2PON_3$ or $N_3CH_2Si(CH_3)_3$. The organolithium or organomagnesium derivatives may be obtained by application or adaptation of the methods described by D. L. Comins et al., J. Org. Chem., 52, 104 (1987); N. Furukana et al., Tetrahedron Lett., 28 (47), 5845 (1987); A. R. Katritzky et al., Org. Prep. Procedure Int., 20 (6), 585 (1988); A. J. Clarke et al., Tetrahedron Lett., 27, 2373 (1974) and A. W. Gschwen et al., Organic Reaction, 26, 1 (1979). The amines for which Rh represents a radical —alk—Het or —alk—Ar" are commercially available or are obtained from the corresponding halides by the action of $NaN(SiCH_3)_3$ or potassium phthalimide, in an inert solvent such as dimethylformamide, in the presence of an organic base such as a trialkylamine or pyridine, at a temperature of between 0° C. and the boiling point of the reaction medium, followed by hydrolysis in acidic medium (for example HCl), at a temperature of between 20° C. and the boiling point of the reaction medium. The amines for which Rh represents a radical —alk—Ar" may also be obtained by application or adaptation of the methods described by J. F. King et al., J. Am. Chem. Soc., 114, 3028 (1992); B. M. Adger et al., Tetrahedron Lett., 25 (45), 5219 (1984); R. Scarpati et al., Gazz. Chim. Ital., 97 (5), 654 (1967).

The derivatives S=C=N—Rh may be obtained from the corresponding primary amines $H_2N$—Rh by the action of thiophosgene, by application or adaptation of the methods described by R. L. Shriner et al., Org. Synth., II, 453, G. M. Dyson, Organic Synth., I, 165, R. J. Slocompie et al., J. Am. Chem. Soc., 72, 1888 (1950) and S. Patai, "The chemistry of cyanates and their thio derivatives", Ed. John Wiley and Sons, pages 619 and 819 (1977).

The compounds of formula (I) for which $R_3$ and $R_4$, together with the carbon atom to which they are attached, form a 2- or 3-pyrrolidine ring, a 2- or 4-piperidine ring or a 2-azacycloheptane ring in which the nitrogen atom is substituted with a radical —CO—alk—$NR_6$—$R_{12}$ in which $R_6$ represents a hydrogen atom and $R_{12}$ represents a radical —CO—NH—alk, may also be prepared by the action of a corresponding compound of formula (I) for which $R_3$ and $R_4$, together with the carbon atom to which they are attached, form a 2- or 3-pyrrolidine ring, a 2- or 4-piperidine ring or a 2-azacycloheptane ring in which the nitrogen atom is substituted with a radical —CO—alk—$NR_6$—$R_{12}$ in which $R_6$ and $R_{12}$ each represent a hydrogen atom, on an alkyl isocyanate.

This reaction is preferably carried out in an inert solvent such as dimethylformamide, tetrahydrofuran or dioxane, at a temperature of between 20° C. and the boiling point of the reaction medium, optionally followed by hydrolysis of the silyl derivative previously obtained, using an aqueous solution, at a temperature of between 20° and 50° C.

The compounds of formula (I) for which R represents a carboxyl radical may also be prepared by hydrolysis of the corresponding compound of formula (I) for which R represents an alkoxycarbonyl radical.

This hydrolysis is preferably carried out either using an inorganic acid (for example hydrochloric acid or sulphuric acid), in aqueous solution, at a temperature of between 20° C. and the boiling point of the reaction medium; or using a base (for example sodium hydroxide, potassium hydroxide or potassium carbonate), in aqueous solution or in aqueous-organic medium (for example water/tetrahydrofuran or water/dioxane), at a temperature of between 0° C. and the boiling point of the reaction medium.

The enantiomers of the compounds of formula (I) may be obtained by resolution of the racemic mixtures, for example by chromatography on a chiral column according to W. H. Pirckle et al., asymmetric synthesis, vol. 1, Academic Press (1983) or by synthesis starting with chiral precursors.

The isomers and diastereoisomers of the compounds of formula (I) may be separated by the usual known methods, for example by crystallization or chromatography.

It is understood by those skilled in the art that, in order to carry out the processes according to the invention which are described above, it may be necessary to introduce protecting groups for the amino, hydroxyl and carboxyl functions in order to avoid side reactions. These groups are those which may be removed without touching the rest of the molecule. Examples of protecting groups for the amino function which may be mentioned are tert-butyl or methyl carbamates, which may be regenerated using iodotrimethylsilane. Examples of protecting groups for the hydroxyl function which may be mentioned are triethylsilyl and benzyl. Protecting groups for the carboxyl functions which may be mentioned are esters (for example the methoxymethyl ester, tetrahydropyranyl ester or benzyl ester), oxazoles and 2-alkyl-1,3-oxazolines. Other protecting groups which may be used are described by W. Greene et al., Protecting Groups in Organic Synthesis, second edition, 1991, John Wiley & Sons.

The compounds of formula (I) may be purified by the usual known methods, for example by crystallization, chromatography or extraction.

The compounds of formula (I) containing a basic residue may optionally be converted into addition salts with an inorganic or organic acid by the action of such an acid in an organic solvent such as an alcohol, a ketone, an ether or a chlorinated solvent.

The compounds of formula (I) containing an acidic residue may optionally be converted into metal salts or into addition salts with nitrogen-containing bases according to methods which are known per se. These salts may be obtained by the action of a metal base (for example an alkali metal or alkaline-earth metal base), ammonia, an amine or an amine salt, on a compound of formula (I), in a solvent. The salt formed is separated out by the usual methods.

These salts also form part of the invention.

Examples of pharmaceutically acceptable salts which may be mentioned are addition salts with inorganic or organic acids (such as acetate, propionate, succinate, benzoate, fumarate, maleate, oxalate, methanesulphonate, isethionate, theophyllinacetate, salicylate, methylene bis-β-oxynaphthoate, hydrochloride, sulphate, nitrate and phosphate), salts with alkali metals (sodium, potassium or lithium) or with alkaline-earth metals (calcium or magnesium), the ammonium salt, and salts of nitrogen-containing bases (ethanolamine, trimethylamine, methylamine, benzylamine, N-benzyl-β-phenethylamine, choline, arginine, leucine, lysine and N-methylglucamine).

The compounds of formula (I) have advantageous pharmacological properties. These compounds are antagonists of the α-amino-3-hydroxy-5-methyl-4-isoxazolepropionic acid (AMPA) receptor, also known as the quisqualate receptor.

Moreover, the compounds of formula (I) are non-competitive antagonists of the N-methyl-D-aspartate (NMDA) receptor and, more particularly, they are ligands for the glycine-modulatory sites of the NMDA receptor.

These compounds are thus useful for treating or preventing all ischemias (such as focal or global ischemia) following cerebrovascular accidents, cardiac arrest, arterial hypotension, cardiac or pulmonary surgical intervention or severe hypoglycaemia. They are also useful in the treatment of effects due to anoxia, whether it be perinatal or following either a drowning or cerebrospinal lesions. These compounds may also be used for treating or preventing the development of neurodegenerative diseases, Huntington's chorea, Alzheimer's disease, amyotrophic lateral sclerosis, olivopontocerebellar atrophy and Parkinson's disease. These compounds may also be used with regard to epileptogenic and/or convulsive symptoms, for the treatment of cerebral or spinal trauma, trauma associated with degeneration of the inner ear (R. Pujol et al., Neuroreport, 3, 299–302 (1992)) or of the retina (J. L. Monsinger et al., Exp. Neurol., 113, 10–17 (1991)), of anxiety (Kehne et al., Eur. J. Pharmacol., 193, 283 (1991)), depression (Trullas et al., Eur. J. Pharmacol., 185, 1 (1990)), schizophrenia (Reynolds, TIPS, 13, 116 (1992)), Tourette's syndrome, hepatic encephalopathies, as analgesics (Dickenson et al., Neurosc. Letters, 121, 263 (1991)), as anti-inflammatory agents (Sluta et al., Neurosci. Letters, 149, 99–102 (1993)), as anti-anorexic agents (Sorrels et al., Brain Res., 572, 265 (1992)), as anti-migraine and anti-emetic agents and for the treatment of poisoning by neurotoxins or other substances which are agonists of the NMDA receptor, as well as neurological problems associated with viral diseases such as AIDS (Lipton et al., Neuron, 7, 111 (1991)), rabies, measles and tetanus (Bagetta et al., Br. J. Pharmacol., 101, 776 (1990)). These compounds are also useful for the prevention of the symptoms of withdrawal from drugs and alcohol, and for inhibiting the addiction to and dependency on opiates. They may also be used in the treatment of deficiencies associated with mitochondrial anomalies such as mitochondrial myopathy, Leber's syndrome, Wernicke's encephalopathy, Rett's syndrome, homocysteinaemia, hyperprolinaemia, hydroxybutyric aminoaciduria, lead encephalopathy and sulphite oxidase deficiency.

The affinity of the compounds of formula (I) for the AMPA receptor was determined by studying the antagonism of the specific binding of |$^3$H|-AMPA to rat cerebral cortex membranes (Honore et al., Neuroscience Letters, 54, 27 (1985)). The |$^3$H|-AMPA is incubated in the presence of 0.2 mg of proteins at 4° C. for 30 minutes in 10 mM KH$_2$PO$_4$ buffer, 100 mM KSCN, pH 7.5. The non-specific binding is determined in the presence of 1 mM L-glutamate. The bound radioactivity is separated by filtration through Pharmacia filters (Printed Filtermate A). The inhibitory activity of these products is less than or equal to 100 µM.

The affinity of the compounds of formula (I) for the glycine site bound to the NMDA receptor was determined by studying the antagonism of the specific binding of |$^3$H|-DCKA to rat cerebral cortex membranes according to the method described by T. Canton et al., J. Pharm. Pharmacol., 44, 812 (1992). The |$^3$H|-DCKA (20 nM) is incubated in the presence of 0.1 mg of proteins at 40° C. for 30 minutes in 50 mM HEPES buffer, pH 7.5. The non-specific binding is determined in the presence of 1 mM glycine. The bound radioactivity is separated by filtration through Whatman GF/B filters. The inhibitory activity of these products is less than or equal to 100 µM.

The compounds of formula (I) are of low toxicity. Their LD$_{50}$ is greater than 50 mg/kg via the IP route in mice.

The preferred compounds of formula (I) are those for which R represents a hydrogen atom or a carboxyl, alkoxycarbonyl or carboxamido radical, R$_1$ and R$_2$ are hydrogen or halogen atoms, R$_3$ and R$_4$, together with the carbon atom to which they are attached, form a 2- or 3-pyrrolidine ring or a 2- or 4-piperidine ring, these rings optionally being substituted on the nitrogen with an alkyl, —COOR$_{11}$, —CO—alk—Ar", —CO—NH—alk, —CO—NH—Ar", —CO—alk, —alk—Ar", —CO—alk—NR$_6$R$_{12}$ or —CO—alk—COOR$_6$ radical or a 2-pyrrolidin-5-one ring. Preferably, in the case of these substituents, R$_{11}$ is an alkyl radical, R$_6$ is a hydrogen atom and R$_{12}$ is a radical —CO—NH—alk.

The following compounds are of particular interest:

(10'RS)-spiro|pyrrolidine-3,10'-5'H,10'H-imidazo|1,2-a|indeno|1,2-e|pyrazine|-4'-one, (10'RS)-spiro|piperidine-2,10'-5'H,10'H-imidazo|1,2-a|indeno|1,2-e|pyrazine|-4'-one, (10'RS)-spiro|pyrrolidine-2,10'-5'H,10'H-imidazo|1,2-a|indeno|1,2-e|pyrazine|-4'-one, (10'RS)-1-methylspiro|pyrrolidine-2,10'-5'H,10'H-imidazo|1,2-a|indeno|1,2-e|pyrazine|-4'-one, (+)-1-methylspiro|pyrrolidine-2,10'-5'H,10'H-imidazo|1,2-a|indeno|1,2-e|pyrazine|-4'-one, (−)-1-methylspiro|pyrrolidine-2,10'-5'H,10'H-imidazo|1,2-a|indeno|1,2-e|pyrazine|-4'-one, (10'RS)-4-oxo-4-{4'-oxo-4',5'-dihydrospiro|pyrrolidine-2,10'-10'H-imidazo|1,2-a|indeno|1,2-e|pyrazin-1-yl|}butyric acid, spiro|piperidine-4,10'-5'H,10'H-imidazo|1,2-a|indeno|1,2-e|pyrazine|-4'-one, 4-oxo-4-{4'-oxo-4',5'-dihydrospiro|piperidine-4,10'-10'H-imidazo|1,2-a|indeno|1,2-e|pyrazin-1-yl|}butyric acid, 1-phenylacetylspiro|piperidine-4,10'-5'H,10'H-imidazo|1,2-a|indeno|1,2-e|pyrazine|-4'-one, 1-(methylcarbamoyl)spiro|piperidine-4,10'-5'H,10'H-imidazo|1,2-a|indeno|1,2-e|pyrazine|-4'-one, 1-methylspiro|piperidine-4,10'-5'H,10'H-imidazo|1,2-a|indeno|1,2-e|pyrazine|-4'-one, 1-benzylspiro|piperidine-4,10'-5'H,10'H-imidazo|1,2-a|indeno|1,2-e|pyrazine|-4'-one, 1-phenethylspiro|piperidine-4,10'-5'H,10'H-imidazo|1,2-a|indeno|1,2-e|pyrazine|-4'-one, (10'RS)-1-acetylspiro|pyrrolidine-2,10'-5'H,10'H-imidazo|1,2-a|indeno|1,2-e|pyrazine|-4'-one, (10'RS)-1-|(3-methylureido)acetyl|spiro|pyrrolidine-2,10'-5'H,10'H-imidazo|1,2-a|indeno|1,2-e|pyrazine|-4'-one, (10'RS)-1-(phenylcarbamoyl)spiro|pyrrolidine-2,10'-5'H,10'H-imidazo|1,2-a|indeno|1,2-e]pyrazine|-4'-one, (10'RS)-1-methyl-8'-fluorospiro|pyrrolidine-2,10'-5'H,10'H-imidazo|1,2-a|indeno|1,2-e]pyrazine|-4'-one, (10'RS)-1-ethylspiro|pyrrolidine-2,10'-5'H,10'H-imidazo|1,2-a|indeno|1,2-e|pyrazine|-4'-one, (10'RS)-1-propylspiro|pyrrolidine-2,10'-5'H,10'H-imidazo|1,2-a|indeno|1,2-e]pyrazine|-4'-one, (10'RS)-4-oxo-4-{4'-oxo-4',5'-dihydrospiro|pyrrolidine-2,10'-10'H-imidazo|1,2-a|indeno|1,2-e|pyrazin-1-yl|}-butyric.

The examples which follow illustrate the invention.

EXAMPLE 1

To a stirred suspension of 2.35 g of 10-methylene-5H, 10H-imidazo|1,2-a|indeno|1,2-e|pyrazin-4-one in 150 ml of dimethylformamide are added, under a stream of argon and at a temperature in the region of 20° C., 2.79 g of N-n- butoxymethyl-N-trimethylsilylmethylbenzylamine dissolved in 25 ml of dimethylformamide, and the stirring is continued until dissolution is complete. 0.1 ml of trifluoroacetic acid is then added and the mixture is left to stir for 3 hours at a temperature in the region of 20° C., and then for 1 hour at 60° C. The dimethylformamide is then removed on a rotavapor and 150 ml of dichloromethane are added to the evaporation residue. The suspension is filtered and the filtrate is evaporated on a rotavapor. The evaporation residue (3 g) is purified by flash chromatography on silica, eluting with a dichloromethane/methanol mixture (96/4 by volume). 1.5 g of (10′RS)-1-benzylspiro[pyrrolidine-3,10′-5′H,10′H-imidazo[1,2-a]indeno[1,2-e]pyrazine]-4′one are obtained in the form of a white solid (Rf=0.43, thin layer chromatography on silica gel, eluent: dichloromethane/methanol (9/1 by volume)); analysis $C_{23}H_{20}N_4O$ % calculated C: 74.98, H: 5.47, N: 15.21, O: 4.34, % found C: 75.0, H: 5.7, N: 15.6, O: 4.8).

10-Methylene-5H,10H-imidazo[1,2-a]indeno[1,2-e]pyrazin-4-one may be prepared in the following way: to a suspension of 19.6 g of 10-hydroxymethyl-5H,10H-imidazo[1,2-a]indeno[1,2-e]pyrazin-4-one in 310 ml of methanol and 39 ml of dimethyl sulphoxide are added, with stirring and under an argon atmosphere, 155 ml of normal aqueous sodium hydroxide solution, and the stirring is continued for 16 hours at a temperature in the region of 20° C. The reaction medium is then acidified with 194 ml of normal aqueous hydrochloric acid solution and the precipitate formed is filtered off, washed with distilled water (2×50 ml), then with acetone (2×50 ml) and dried, first in air and then under vacuum (2 mm Hg; 0.26 kPa) at 60° C. 14 g of 10-methylene-5H,10H-imidazo[1,2-a]indeno[1,2-e]pyrazin-4-one are thus obtained in the form of a yellow solid (Rf=0.53, thin layer chromatography on silica gel, eluent: chloroform/methanol (8/2 by volume)).

10-Hydroxymethyl-5H,10H-imidazo[1,2-a]indeno[1,2-e]pyrazin-4-one may be prepared in the following way: to a suspension of 3 g of 10-hydroxymethylene-5H,10H-imidazo[1,2-a]indeno[1,2-e]pyrazin-4-one (mixture of the Z and E forms) in 240 ml of methanol is added portionwise over 10 minutes, with stirring, 1 g of sodium borohydride, and the stirring is continued at a temperature in the region of 20° C. for 1 hour 30 minutes. A further 1 g of sodium borohydride is added portionwise and the stirring is continued for 30 minutes. The reaction mixture is then filtered and the filter is rinsed with twice 30 ml of methanol. The insoluble material is taken up in 50 ml of water and 4 ml of 1N hydrochloric acid, filtered again, washed with water until neutral and air-dried. The crude product (1 g) is purified by hot dissolution into 65 ml of dimethylformamide, filtration, addition of 80 ml of methanol to the filtrate while still hot and crystallization in an ice-water bath. The crystals obtained are filtered off, washed with twice 15 ml of methanol and dried at 80° C. 0.66 g of 10-hydroxymethyl-5H,10H-imidazo[1,2-a]indeno-[1,2-e]pyrazin-4-one is thus obtained in the form of a white solid melting above 260° C. (analysis % calculated C: 66.40, H: 4.38, N: 16.59, O: 12.63, % found C: 66.4, H: 4.3, N: 16.6, O: 12.1).

10-Hydroxymethylene-5H,10H-imidazo[1,2-a]indeno[1,2-e]pyrazin-4-one may be prepared in the following way: a solution of 1.4 g of 10-(E)-dimethylaminomethylene-5H,10H-imidazo[1,2-a]indeno[1,2-e]pyrazin-4-one in 35 ml of 5N hydrochloric acid is stirred for 30 minutes at a temperature in the region of 25° C. After addition of 60 ml of distilled water and neutralization with 120 ml of saturated aqueous sodium hydrogen carbonate solution, the solid formed is separated out by filtration, washed twice with 60 ml in total of distilled water and air-dried. The product obtained (1.1 g) is dissolved in 120 ml of dimethyl sulphoxide and, after addition of 120 ml of distilled water, the solid formed is separated out by filtration, washed twice with 10 ml in total of distilled water and twice with 10 ml in total of acetone and then dried under reduced pressure (1 mm Hg; 0.13 kPa) at 100° C. 1 g of 10-hydroxymethylene-5H,10H-imidazo[1,2-a]indeno[1,2-e]pyrazin-4-one, is thus obtained as a 40/60 mixture of the Z and E forms, decomposing without melting at 290° C. [NMR spectrum: (200 MHz; DMSO-$d_6$; δ in ppm): a 40/60 mixture of isomers is observed: from 7.20 to 7.40 (mt, 2H: —H7 and —H8); 7.56 and 7.64–8.29 and 8.79 (4 broad s, 2×1H: —H of the imidazole); from 7.80 to 8.15 (mt, 2H: —H6 and —H9); 8.21 and 8.24 (2s, 1H in total: =CH—O—); 12.43 (unres. mult., 1H: —NH—)].

10-(E)-Dimethylaminomethylene-5H,10H-imidazo[1,2-a]indeno[1,2-e]pyrazin-4-one may be prepared in the following way: 6.3 g of t-butoxybis(dimethylamino)methane are added dropwise, at a temperature in the region of 25° C. and over 5 minutes, to a suspension of 5.5 g of 5H,10H-imidazo[1,2-a]indeno[1,2-e]pyrazin-4-one in 100 ml of dimethylformamide. After stirring for 30 minutes at the same temperature, the mixture is poured into 500 ml of distilled water and extracted 5 times with 1.5 liters in total of chloroform. The organic extracts are combined, washed with 250 ml of distilled water, dried over anhydrous magnesium sulphate and concentrated to dryness under reduced pressure (15 mm Hg; 2 kPa) at 60° C. The product obtained (4.5 g) is suspended in 25 ml of methanol, filtered, washed twice with 20 ml in total of methanol and dried under reduced pressure (15 mm Hg; 2 kPa) at 20° C. The product obtained (4.5 g) is dissolved in 45 ml of boiling dimethylformamide and the solution, after cooling, is stored for 4 hours at a temperature in the region of 5° C. The crystals are separated off by filtration, washed successively with 10 ml of dimethylformamide, 10 ml of acetone and dried to dryness under reduced pressure (1 mm Hg; 0.13 kPa) at 100° C. 4 g of 10-(E)-dimethylaminomethylene-5H,10H-imidazo-[1,2-a]indeno[1,2-e]pyrazin-4-one melting at 293° C. are thus obtained [NMR spectrum: (200 MHz; DMSO-$d_6$; δ in ppm): 3.35 [s, 6H: —N(CH$_3$)$_2$]; 7.18 and 7.28 (2t, J=7.5 Hz, 2H: —H7 and —H8); 7.48 and 7.92 (2d, J=7.5 Hz, 1H each: —H6 and —H9); 7.63 and 8.50 (2 broad s, 1H each: —H of the imidazole); 8.09 (s, 1H: =CH—N); 12.30 (unres. mult., 1H: —NH—)].

5H,10H-Imidazo[1,2-a]indeno-[1,2-e]pyrazin-4-one may be prepared in the following way: a solution of 4.8 g of 3-methyl-4-oxo-5H,10H-imidazo[1,2-a]indeno-[1,2-e]pyrazinium bromide in 30 g of imidazole is heated for 24 hours at 160° C., cooled to 100° C. and then poured into a stirred mixture of 75 g of ice and 75 g of distilled water. The insoluble material is filtered off, washed twice with 20 ml in total of distilled water and then dried under reduced pressure (10 mm Hg; 1.3 kPa) at 50° C. The product thus obtained (4 g) is dissolved in 80 ml of dimethylformamide and, after addition of 20 g of silica, the solution is concentrated to dryness under reduced pressure (15 mm Hg; 2 kPa) at 100° C. The mixture is introduced into a column 4.2 cm in diameter containing 240 g of silica and is then eluted with a dichloromethane/methanol mixture (97/3 by volume), collecting 60 ml fractions. Fractions 10 to 70 are combined, 1.5 g of decolorizing charcoal are added and the mixture is filtered and concentrated to dryness under reduced pressure (15 mm Hg; 2 kPa) at 55° C. The product obtained (1.7 g) is dissolved in 350 ml of boiling methanol and, after addition of 0.1 g of decolorizing charcoal, the solution is filtered while hot, concentrated under reduced pressure (15 mm Hg; 2 kPa) at 40° C. in order to bring its volume to about 30 ml, and is then stored at 5° C. for 60 hours. The crystals are separated out by filtration, washed twice with 20 ml in total of ice-cold methanol and dried under reduced pressure (1 mm Hg; 0.13 kPa) at 60° C. 1.1 g of 5H,10H-imidazo|1,2-a|-indeno|1,2-e|pyrazin-4-one are thus obtained, decomposing without melting at 3500° C. |Rf=0.77, thin layer chromatography on silica gel, solvent: dichloromethane/methanol (8/2 by volume)|.

3-Methyl-4-oxo-5H,10H-imidazo|1,2-a|indeno|1,2-e|pyrazinium bromide may be prepared in the following way: a solution of 5 g of 1-methyl-1H-imidazole-2-carboxamide and 12 g of 2-bromoindanone at a concentration of 85% in 100 ml of anhydrous dimethylformamide is stirred for 28 hours at 115° C. and then cooled to a temperature in the region of 20° C. The insoluble material is separated out by filtration, washed twice with 20 ml in total of ice-cold dimethylformamide and dried under reduced pressure (10 mm Hg; 1.3 kPa). 4.8 g of 3-methyl-4-oxo-5H,10H-imidazo |1,2-a|indeno|1,2-e|pyrazinium bromide are thus obtained |NMR spectrum: (200 MHz; DMSO-$d_6$; $\delta$ in ppm): 4.13 (s, 2H: —$CH_2$ at 10); 4.34 (s, 3H: $N^+$ —$CH_3$); 7.47 (mt, 2H: —H7 and —H8); 7.68 and 7.96 (2d, J=7.5 Hz, 1H each; —H6 and —H9); 8.32 and 8.45 (2d, J=1 Hz, 1H each; H of the imidazole); 13.60 (unres. mult., 1H: NH)|.

1-Methyl-1H-imidazole-2-carboxamide may be prepared according to the process described by D. D. Davey, J. Org. Chem., 52 4379 (1987).

N-n-Butoxymethyl-N-trimethylsilylmethylbenzylamine may be prepared according to the method described by Y. Terao et al., Chem. Pharm. Bull., 33, 2762 (1985).

EXAMPLE 2

A mixture of 1 g of (10'RS)-1-benzylspiro|pyrrolidine-3, 10'-5'H,10'H-imidazo|1,2-a|indeno|1,2-e|pyrazine|-4'-one, 50 ml of acetic acid and 0.2 g of 20% palladium hydroxide-on-charcoal is hydrogenated, in an auatoclave at a temperature in the region of 60° C. and at a pressure of 10 bar, for 3 hours. After removal of the catalyst under inert atmosphere, the reaction mixture is evaporated on a rotavapor and the evaporation residue is dissolved in water. The aqueous solution is neutralized with sodium hydrogen carbonate solution to give a precipitate which is filtered off, washed with distilled water and dried at 35° C. under vacuum (1 mm Hg; 0.13 kPa). 0.25 g of (10'RS)-spiro |pyrrolidine-3,10'-5'H,10'H-imidazo|1,2-a|indeno|1,2-e| pyrazine|-4'-one is obtained in the form of a cream-coloured solid melting above 260° C. (analysis % calculated C: 69.05, H: 5.07, N: 20.13, O: 5.75. % found C: 69.2, H: 5.0, N: 19.7, O: 5.0).

EXAMPLE 3

To a stirred suspension of 1.7 g of 10-tert-butoxycarbonylamino-5H,10H-imidazo|1,2-a|indeno|1,2-e| pyrazin-4-one in 15 ml of dimethyl sulphoxide is added portionwise 0.6 g of 80% sodium hydride and the stirring is continued for 15 minutes. 0.63 ml of 1 bromo-4-chlorobutane dissolved in 1.5 ml of dimethylformamide is added over 3 minutes to the brown solution obtained, and the mixture is left stirring for 2 hours 30 minutes at a temperature in the region of 20° C. The reaction medium is poured onto a mixture of 50 g of crushed ice, 100 ml of distilled water and 2 ml of acetic acid. The suspension obtained is filtered and the insoluble material is washed with distilled water (2×20 ml), then with 20 ml of acetone and air-dried overnight. 1.37 g of (10'RS)-1-tert-butoxycarbonylspiro |piperidine-2,10'-5'H,10'H-imidazo|1,2-a|indeno|1,2-e| pyrazine|-4'-one are obtained in the form of a cream-coloured solid melting above 260° C. (Rf=0.86, thin layer chromatography on silica gel, eluent: chloroform/methanol/ 28% aqueous ammonia (12/3/0.5 by volume)). Deprotection of the NH is carried out in the following way: to 11 ml of trifluoroacetic acid are added portionwise, with stirring, 1.36 g of (10'RS)-1-tert-butoxycarbonylspiro|piperidine-2,10'-5'H,10'H-imidazo|1,2-a|indeno|1,2-e|-pyrazine|-4'-one and the stirring is continued at a temperature in the region of 20° C. for 2 hours 30 minutes. The reaction medium is evaporated on a rotavapor and the evaporation residue is treated with 35 ml of distilled water and neutralized to pH 7 by portionwise addition of sodium hydrogen carbonate. The suspension obtained is filtered and the insoluble material is washed with distilled water (3×20 ml) and then with 20 ml of isopropanol. After drying at 60° C. under vacuum (1 mm Hg; 0.13 kPa), 0.9 g of (10'RS)-spiro|piperidine-2,10'-5'H, 10'H-imidazo|1,2-a|indeno-|1,2-e|pyrazine|-4'-one is obtained in the form of a pale pink solid melting at 268° C. with decomposition (analysis % calculated C: 69.85, H: 5.52, N: 19.16, O: 5.47, % found C: 69.8, H: 5.8, N: 19.4).

10-tert-Butoxycarbonylamino-5H,10H-imidazo|1,2-a| indeno|1,2-e|pyrazin-4-one may be prepared in the following way: to a stirred suspension of 39.2 g of 10-amino-5H, 10H-imidazo|1,2-a|indeno|1,2-e|pyrazin-4-one hydrochloride in 400 ml of dimethylformamide are added, at a temperature in the region of 30° C. and under a stream of nitrogen, 22.4 g of di-tert-butyl dicarbonate followed by a solution of 25 ml of triethylamine in 35 ml of dimethylformamide, and the stirring is continued for 20 hours. The reaction mixture is filtered and the insoluble material is washed with 50 ml of dimethylformamide, then with distilled water (3×100 ml) and finally with 100 ml of acetone. After drying in air and then under vacuum (1 mm Hg; 0.13 kPa) at 100° C., 30.6 g of 10-tert-butoxycarbonylamino-5H,10H-imidazo|1,2-a|indeno|1,2-e| pyrazin-4-one are obtained in the form of a pale yellow solid melting above 260° C. (Rf=0.64, thin layer chromatography on silica gel, eluent: chloroform/methanol/28% aqueous ammonia (12/3/0.5 by volume)).

10-Amino-5H,10H-imidazo|1,2-a|indeno|1,2-e|pyrazin-4-one may be prepared in the following way: a solution of 12.9 g of 10-acetamido-5H,10H-imidazo|1,2-a|indeno|1,2-e|pyrazin-4-one in 650 ml of aqueous 2N hydrochloric acid solution is heated to boiling for 2 hours, cooled and then concentrated to dryness under reduced pressure (15 mm Hg; 2 kPa) at 80° C. 4 g (out of the 14.8 g obtained in total) are dissolved in 250 ml of distilled water and the solution is stirred for 16 hours at a temperature in the region of 20° C. The crystals formed are separated out by filtration, washed successively with 25 ml of distilled water and 25 ml of methanol and then air-dried at a temperature in the region of 20° C. The product obtained (3.5 g) is stirred in suspension for 10 minutes in 100 ml of boiling methanol and, after cooling and storing for 1 hour at 5° C., is isolated by filtration, washed with 20 ml of ice-cold methanol and then dried under reduced pressure (1 mm Hg; 0.13 kPa) at 100° C. 2.1 g of 10-amino-5H,10H-imidazo|1,2-a|indeno-|1,2-e| pyrazin-4-one are thus obtained, decomposing without melting at about 240° C. |NMR spectrum: (200 MHz; DMSO-$d_6$; $\delta$ in ppm): 5.70 (broad s, 1H: CH—$N^+Cl^-$); 7.48 and 7.58 (2t, J=7.5 Hz, 1H each: —H7 and —H8); 7.72 and 8.76 (2s, 1H each: —H of the imidazole); 7.98 and 8.09 (2d, J=7.5 Hz, 1H each: —H6 and —H9); 9.47 (unres. mult., 3H: $N^+H_3$ $Cl^-$); 12.80 (unres. mult., 1H: —NH—)|.

10-Acetamido-5H,10H-imidazo[1,2-a]indeno[1,2-e]pyrazin-4-one may be prepared in the following way: a suspension of 5.25 g of 10-(E-hydroxyimino)-5H,10H-imidazo[1,2-a]indeno[1,2-e]pyrazin-4-one and 2.9 g of zinc powder in 100 ml of acetic acid is heated for 2 hours at a temperature of between 80° C. and 90° C. After addition of 100 ml of acetic acid, the mixture is filtered and the filtrate is concentrated to dryness under reduced pressure (10 mm Hg; 2 kPa) at 65° C. The product obtained (3.8 g) is suspended in 100 ml of distilled water, filtered, washed with 10 ml of distilled water and with 10 ml of acetone and then dried under reduced pressure (15 mm Hg; 2 kPa) at 20° C. The product obtained (2 g) is dissolved in 60 ml of boiling dimethylformamide and, after addition of 0.1 g of decolorizing charcoal, the solution is filtered while hot. The filter is washed with 10 ml of boiling dimethylformamide and the filtrate and combined washings are then stored for 4 hours at a temperature in the region of 20° C. The crystals formed are separated out by filtration, washed successively with 10 ml of dimethylformamide, 10 ml of distilled water, 10 ml of acetone and dried to dryness under reduced pressure (1 mm Hg; 0.13 kPa) at 100° C. 0.43 g of 10-acetamido-5H,10H-imidazo[1,2-a]indeno[1,2-e]pyrazin-4-one is thus obtained, decomposing without melting at 330° C. [NMR spectrum: (200 MHz; DMSO-$d_6$; δ in ppm): 2.00 (s, 3H: —CO—CH$_3$); 6.13 (d, J=8.5 Hz, 1H: CH—N); 7.35 and 7.48 (2t, J=7.5 Hz, 1H each: —H7 and —H8); 7.48 and 7.85 (2d, J=7.5 Hz, 1H each: —H6 and —H9); 7.58 and 7.65 (2 broad s, 1H each: —H of the imidazole); 8.58 (d, J=8.5 Hz, 1H: —NH—COCH$_3$); 12.50 (unres. mult., 1H: —NH—)].

10-(E-Hydroxyimino-5H,10H-imidazo[1,2-a]indeno[1,2-e]pyrazin-4-one may be prepared in the following way: 0.4 of 80% sodium hydride is added to a suspension of 1.1 g of 5H,10H-imidazo[1,2-a]indeno[1,2-e]pyrazin-4-one in 10 ml of anhydrous dimethyl sulphoxide. After stirring for 10 minutes at a temperature in the region of 20° C., a solution of 0.7 g of isoamyl nitrite in 2 ml of anhydrous dimethyl sulphoxide is added dropwise over 5 minutes and the mixture is then stirred for 1 hour at the same temperature. 10 ml of distilled water are added slowly and the mixture is then poured into 120 g of ice-water, acidified with 1 ml of acetic acid and then centrifuged. After removal of the supernatant solution, the solid is suspended in 25 ml of distilled water, filtered, washed with 10 ml of acetone and dried under reduced pressure (15 mm Hg; 2 kPa) at 20° C. The product obtained (1.5 g) is dissolved in 100 ml of boiling dimethylformamide and, after addition of 0.1 g of decolorizing charcoal, the solution is filtered while hot, cooled, poured into 800 ml of distilled water and centrifuged. The solid is suspended in 20 ml of distilled water, filtered, washed with 20 ml of acetone and dried under reduced pressure (15 mm Hg; 2 kPa) at 20° C. The product obtained (0.9 g) is dissolved in 75 ml of dimethyl sulphoxide at 20° C. and, after addition of 0.1 g of decolorizing charcoal, the solution is filtered. The filter is washed twice with 20 ml in total of dimethyl sulphoxide and the filtrate and washings are then combined. 75 ml of distilled water are added and the mixture is centrifuged. The solid is suspended in 25 ml of distilled water, filtered, washed twice with 50 ml in total of acetone and then dried under reduced pressure (1 mm Hg; 0.13 kPa) at 60° C. 0.63 g of 10-(E-hydroxyimino)-5H,10H-imidazo [1,2-a]indeno[1,2-e]pyrazin-4-one is thus obtained, decomposing without melting above 300° C. [NMR spectrum: (200 MHz; DMSO-$d_6$; δ in ppm): 7.40 and 7.48 (2t, J=7 Hz, 2H: —H7 and —H8); 7.60 and 8.00 (2 broad s, 1H each: —H of the imidazole); 7.82 and 8.20 (2d, J=7 Hz, 1H each: —H6 and —H9); 12.70 and 13.00 (2 unres. mult., 1H each: —NH— and OH)].

EXAMPLE 4

The process is performed as in Example 3 but starting with 0.7 g of 10-tert-butoxycarbonylamino-5H,10H-imidazo[1,2-a]indeno[1,2-e]pyrazin-4-one, 20.5 ml of dimethyl sulphoxide, 0.24 g of 80% sodium hydride and 0.22 ml of 1-bromo-3-chloropropane. After hydrolysis, the reaction medium is subjected to extractions with ethyl acetate (4×200 ml). The organic phases are combined; they contain an insoluble material which is filtered off, washed with 10 ml of distilled water and then with 10 ml of ethyl acetate and air-dried to give 0.29 g of crude product (A). The organic phases are combined, washed with distilled water (150 ml) and evaporated on a rotavapor. The evaporation residue (0.41 g) is triturated with 5 ml of acetone, filtered, washed with 2 ml of acetone and air-dried to give 0.18 g of crude product (B). The crude products (A) and (B) are combined and purified by flash chromatography on silica, eluting with a chloroform/methanol/28% aqueous ammonia mixture (12/2.25/0.38 by volume). 0.43 g of (10'RS)-1-tert-butoxycarbonylspiro[pyrrolidine-2,10'-5'H,10'H-imidazo[1,2-a]indeno[1,2-e]pyrazine]-4'-one is obtained in the form of a cream-coloured solid melting above 260° C. (analysis C$_{21}$H$_{22}$N$_4$O$_3$ % calculated C: 66.65, H: 5.86, N: 14.81, O: 12.68, % found C: 67.0, H: 5.1, N: 14.5).

EXAMPLE 5

To 6 ml of trifluoroacetic acid are added portionwise, with stirring, 0.42 g of (10'RS)-1-tert-butoxycarbonylspiro [pyrrolidine-2,10'-5'10'H-imidazo[1,2-a]indeno[1,2-e] pyrazine]-4'-one and the stirring is continued at a temperature in the region of $_{20}$° C. for 2 hours 30 minutes. The reaction medium is evaporated on a rotavapor and the evaporation residue is treated with 15 ml of distilled water and neutralized at pH 7 by portionwise addition of sodium hydrogen carbonate. The suspension obtained is filtered and the insoluble material is washed with distilled water (3×20 ml) and then with 20 ml of isopropanol. After drying at 60° C. under vacuum (1 mm Hg; 0.13 kPa), 0.15 g of (10'RS) -spiro[pyrrolidine-2,10'-5'H,10'H-imidazo[1,2-a]indeno[1,2-e]pyrazine]-4'-one is obtained in the form of a cream-coloured solid decomposing at about 260° C. on a Maquenne block (analysis % calculated C: 69.05, H: 5.07, N: 20.13, O: 5.75, % found C: 69.4, H: 5.0, N: 19.7).

EXAMPLE 6

A mixture of 3 ml of 37% formaldehyde solution, 1.1 g of (10'RS)-spiro[pyrrolidine-2,10'-5'H,10'H-imidazo[1,2-a] indeno[1,2-e]pyrazine]-4'-one and 1.5 ml of formic acid is stirred for 1 hour at a temperature in the region of 28° C. The solution obtained is then evaporated on a rotavapor. The evaporation residue is triturated with 60 ml of distilled water, filtered, washed with distilled water (4×5 ml) and air-dried. After drying at 60° C. under vacuum (1 mm Hg; 0.13 kPa) 0.62 g of (10'RS)-1-methylspiro[pyrrolidine-2, 10'-5'H,10'H-imidazo[1,2-a]indeno-[1,2-e]pyrazine]-4'-one is obtained in the form of a cream-coloured solid melting at 230° C. with decomposition on a Maquenne block [$^1$H NMR spectrum (200 MHz, (CD$_3$)$_2$SO-$d_6$ with addition of a few drops of CD$_3$COOD-$d_4$, δ in ppm): from 1.70 to 2.10 and from 2.20 to 2.70 (2 mts, 2H each: CH$_2$CH$_2$); 1.82 (s, 3H: NCH$_3$); from 3.00 to 3.50 (mt, 2H: NCH$_2$); from 7.20 to 7.50 and 7.85 (mt and d respectively (J=7.5 Hz), 3H and 1H: aromatic H); 7.60 and 7.90 (2s, 1H each: H of the imidazole)].

EXAMPLE 7

By chromatography of 4 times 0.8 g of (±)-1-methylspiro [pyrrolidine-2,10'-5'H,10'H-imidazo[1,2-a]indeno[1,2-e]

pyrazine|-4'-one on a CHIRACEL OC type chiral column (length=250 mm; diameter=60 mm), using absolute ethanol at a flow rate of 30 ml/minute as eluent, 1.40 g of (+)-1-methylspiro|pyrrolidine-2,10'-5'H,10'H-imidazo|1,2-a| indeno|1,2-e|pyrazine|-4'-one in the form of a cream-coloured solid | $|\alpha|_D^{20}$=+32.4 (acetic acid; c=0.5%)| and 1.36 g of (−)-1-methylspiro|pyrrolidine-2,10'-5'H,10'H-imidazo|1,2-a|indeno|1,2-e|pyrazine|-4'-one in the form of a cream-coloured solid | $|\alpha|_D^{20}$=−32.0 (acetic acid; c=0.5%)| are obtained.

EXAMPLE 8

To a stirred solution of 0.7 g of (10'RS)-spiro|pyrrolidine-2,10'-5'H,10'H-imidazo|1,2-a|indeno-|1,2-e|pyrazine|-4'-one in 8 ml of acetic acid is added 0.6 g of succinic anhydride and the stirring is continued for 48 hours at a temperature in the region of 20° C. The suspension obtained is filtered and the insoluble material is washed with 3 ml of acetic acid, then with distilled water (3×3 ml) and finally with 3 ml of acetone. After drying at 60° C. under vacuum (1 mm Hg; 0.13 kPa), 0.28 g of (10'RS)-4-oxo-4-{4'-oxo-4',5'-dihydrospiro|pyrrolidine-2,10'-10'H-imidazo|1,2-a| indeno|1,2-e|pyrazin-1-yl|}butyric acid is obtained in the form of a cream-coloured solid melting at 300° C. with decomposition on a Maquenne block |$^1$H NMR spectrum (200 MHz, $(CD_3)_2SO$-$d_6$ with addition of a few drops of $CD_3COOD$-$d_4$, at a temperature of 373 K., δ in ppm): from 1.80 to 2.70 (mts, 8H: $CH_2$); 4.15 (mt, 2H: $NCH_2$); from 7.20 to 7.60 and 7.85 (mt and d respectively (J=7.5 Hz), 3H and 1H: aromatic H); 7.55 and 7.59 (2s, 1H each: H of the imidazole)|.

EXAMPLE 9

To a suspension of 0.89 g of 5H,10H-imidazo|1,2-a| indeno|1,2-e|pyrazine|-4'-one in 10 ml of dimethyl sulphoxide, under nitrogen, is added a solution of 1.18 g of N,N-bis(2-chloroethyl)-p-toluenesulphonamide in 5 ml of dimethyl sulphoxide, followed by progressive addition, with vigorous stirring, of 0.8 g of 60% sodium hydride over about 30 minutes. The stirring is continued for 20 hours at a temperature in the region of 20° C. After addition of methanol and then water, the mixture is poured into ice and acidified with 1N hydrochloric acid. The insoluble material is filtered off, washed with absolute ethanol and dried under reduced pressure (1 mm Hg; 0.13 kPa) at 50° C. to give 0.9 g of 1-tosylspiro|piperidine-4,10'-5'H,10'H-imidazo|1,2-a| indeno|1,2-e|pyrazin|-4'-one, the melting point of which is above 260° C. |$^1$H NMR spectrum (400 MHz, $(CD_3)_2SO$-$d_6$ with addition of a few drops of $CD_3COOD$-$d_4$, at a temperature of 333 K., δ in ppm): 1.42 (broad d, J=14 Hz, 2H: equatorial H of the $CH_2$ of the piperidine); 2.50 (mt, 2H: axial H of the $CH_2$ of the piperidine); 2.52 (s, 3H: Ar$CH_3$); 3.27 (broad t, J=14 Hz, 2H: axial H of the $NCH_2$ of the piperidine); 3.97 (broad d, J=14 Hz, 2H: equatorial H of the $NCH_2$ of the piperidine); from 7.20 to 8.00 (mt, 10H: aromatic H and H of the imidazole)|, the NH of which is then deprotected in the following way: a suspension of 0.9 g of 1-tosylspiro|piperidine-4,10'-5'H,10'H-imidazo|1,2-a| indeno|1,2-e|pyrazine|-4'-one in 20 ml of 47% hydrobromic acid is maintained at reflux for 5 hours. After cooling to a temperature in the region of 20° C. and addition of about 20 ml of distilled water, the reaction medium is neutralized with concentrated aqueous sodium hydroxide. The precipitate is filtered off and taken up in 1N hydrochloric acid, the insoluble material is discarded and the filtrate is neutralized with concentrated aqueous sodium hydroxide. The precipitate is filtered off, washed with water and dried under reduced pressure (1 mm Hg; 0.13 kPa) at 50° C. 0.1 g of spiro|piperidine-4,10'-5'H,10'H-imidazo|1,2-a|indeno|1,2-e|pyrazine|-4'-one hydrochloride is thus obtained in the form of a green powder, the melting point of which is above 260° C. |$^1$H NMR spectrum (400 MHz, $(CD_3)_2SO$-$d_6$ with addition of a few drops of $CD_3COOD$-$d_4$, δ in ppm): 1.55 (broad d, J=14 Hz, 2H: equatorial H of the $CH_2$ of the piperidine); 2.92 (dt, J=14 and 5.5 Hz, 2H: axial H of the $CH_2$ of the piperidine); from 3.50 to 3.75 (mt 4H: $NCH_2$ of the piperidine); from 7.30 to 8.05 (mt, 4H: aromatic H); 7.62 and 8.65 (2 s, 1H each: H of the imidazole)|.

EXAMPLE 10

A mixture of 373 mg of spiro|piperidine-4,10'-5'H,10'H-imidazo|1,2-a|indeno|1,2-e|pyrazine|-4'-one hydrobromide, 20 ml of dioxane, 0.14 ml of triethylamine, 110 mg of succinic anhydride and 135 mg of 4-dimethylaminopyridine is heated at reflux for 2 hours. The reaction mixture is filtered and the solid obtained is washed with 1N hydrochloric acid, then with water (4×5 ml) and finally with ethyl ether. After drying at 35° C. under vacuum (1 mm Hg; 0.13 kPa), 180 mg of 4-oxo-4-{4'-oxo-4',5'-dihydrospiro|piperidine-4,10'-10'H-imidazo|1,2-a|indeno |1,2-e|pyrazin|-1-yl|}butyric acid are obtained in the form of a greyish solid melting above 260° C. (analysis $C_{21}H_{20}N_4O_4$ % calculated C: 64.28, H: 5.14, N: 14.28, O: 16.31, % found C: 64.3, H: 5.2, N: 14.3).

EXAMPLE 11

To a stirred mixture, at a temperature in the region of 20° C., of 730 mg of spiro|piperidine-4,10'-5'H,10'H-imidazo|1,2-a|indeno|1,2-e|pyrazine|-4'-one and 15 ml of dimethylformamide is added dropwise 0.42 ml of triethylamine. The reaction medium is cooled to about 5° C. and a solution of 0.21 ml of acetyl chloride in 10 ml of dimethylformamide is added dropwise. The stirring is continued overnight, allowing the temperature of the reaction mixture to rise to about 20° C., and 15 ml of water are added. The reaction mixture is subjected to 4 extractions with dichloromethane (140 ml in total) and the organic phase is washed with distilled water (3×20 ml), dried over magnesium sulphate, filtered and evaporated on a rotavapor. 100 mg of 1-acetylspiro |piperidine-4,10'-5'H,10'H-imidazo|1,2-a|indeno|1,2-e| pyrazine|-4'-one are obtained in the form of a yellow solid melting above 260° C. |NMR spectrum: (250 MHz, DMSO-$d_6$; δ in ppm): 1.35 and 1.42 (d, J=12 Hz, 1H: eq. CH); 2.18 (s, 3H, $COCH_3$); 2.30 and 2.55 (m, 1H, ax. CH); 3.28 and 3.82 (t, J=12 Hz, 1H: ax. NCH); 4.04 and 4.65 (d, J=12 Hz, 1H: eq. NCH); 7.35 (t, J=7 Hz, 1H: arom. CH); 7.48 (t, J=7 Hz, 1H: arom. CH); 7.62 (s, 1H: arom. CH); 7.97 (d, J=7 Hz, 1H: arom. CH); 8.09 (d, J=7 Hz, 1H: arom. CH); 8.15 (s, 1H: arom. CH); 12.42 (s, 1H: NH)|.

EXAMPLE 12

The process is performed as in Example 11 but starting with 746 mg of spiro|piperidine-4,10'-5'H,10'H-imidazo|1, 2-a|indeno|1,2-e|pyrazine|-4'-one hydrobromide, 0.62 ml of triethylamine and 0.29 ml of phenylacetyl chloride. The evaporation residue is in the form of a brown oil. After trituration in acetonitrile, this oil gives a precipitate which is filtered off, washed with acetonitrile and dried at 40° C. under vacuum (1 mm Hg; 0.13 kPa). 390 mg of 1-phenylacetylspiro|piperidine-4,10'-5'H,10'H-imidazo|1,2-a|indeno|1,2-e|pyrazine|-4'-one are thus obtained in the form of a light grey solid melting above 260° C. (analysis $C_{25}H_{22}N_4O_2$ % calculated C: 73.15, H: 5.40, N: 13.65, O: 7.80, % found C: 72.8, H: 5.5, N: 14.0, O: 7.7).

EXAMPLE 13

The process is performed as in Example 11 but starting with 1 g of spiro[piperidine-4,10'-5'H,10'H-imidazo[1,2-a]indeno[1,2-e]pyrazine]-4'-one hydrobromide, 40 ml of dimethylformamide, 0.75 ml of triethylamine and 0.44 ml of hydrocinnamoyl chloride. 170 mg of 1-(3-phenylpropionyl)spiro[piperidine-4,10'-5'H,10'H-imidazo[1,2-a]indeno[1,2-e]pyrazine]-4'-one are obtained in the form of a beige-coloured solid melting at about 232° C. with decomposition [NMR spectrum: (200 MHz; DMSO-$d_6$+$CD_3CO_2D$; δ in ppm): 1.40 (d, J=14 Hz, 1H: eq. CH); between 2.5 and 3.00 (m, 5H: ax. CH and 2 $CH_2$); 3.30 and 3.75 (t, J=14 Hz, 1H: ax. NCH); 4.10 and 4.70 (d, J=14 Hz, 1H: eq. NCH); 7.23 (t, J=7 Hz, 1H: arom. CH); between 7.25 and 7.40 (m, 5H: phenyl H); 7.45 (t, J=7 Hz, 1H: arom. CH); 7.61 (s, 1H: arom. CH); 7.95 (s, 1H: arom. CH); 7.97 (d, J=7 Hz, 1H: arom. CH); 8.03 (d, J=7 Hz, 1H: arom. CH)].

EXAMPLE 14

The process is performed as in Example 11 but starting with 1.1 g of spiro[piperidine-4,10'-5'H,10'H-imidazo[1,2-a]indeno[1,2-e]pyrazine]-4'-one hydrobromide, 40 ml of dimethylformamide, 1.25 ml of triethylamine and 600 mg of 3-diethylaminopropionyl chloride hydrochloride. The reaction medium is concentrated on a rotavapor and the evaporation residue is chromatographed on a column of silica, eluting with a dichloromethane/methanol mixture (95/5 by volume) and then with methanol alone. The methanol eluate (600 mg) is purified on a column of silica, eluting with a dichloromethane/methanol mixture (90/10 by volume). 400 mg of 1-(3-diethylaminopropionyl)spiro[piperidine-4,10'-5'H,10'H-imidazo[1,2-a]indeno[1,2-e]pyrazine]-4'-one are obtained in the form of a beige-coloured foam [mass spectrum: (D/CI; reagent gas: ammonia): M/Z=420 ($MH^+$)].

3-Dimethylaminopropionyl chloride may be obtained as described in patent DE 2,550,566.

EXAMPLE 15

To a stirred solution of 1 g of spiro[piperidine-4,10'-5'H,10'H-imidazo[1,2-a]indeno[1,2-e]pyrazine]-4'-one hydrobromide in 25 ml of dimethylformamide is added 0.38 ml of triethylamine and the stirring is continued for 30 minutes, followed by dropwise addition of 0.32 ml of methyl isocyanate. The stirring is continued overnight at a temperature in the region of 20° C. The reaction medium is filtered and the solid obtained is washed with dimethylformamide, then with distilled water and finally with ethyl ether. After drying at 35° C. under vacuum (1 mm Hg; 0.13 kPa), 250 mg of 1-(methylcarbamoyl)spiro[piperidine-4,10'-5'H,10'H-imidazo[1,2-a]indeno[1,2-e]pyrazine]-4'-one are obtained in the form of a white solid melting above 260° C. (analysis $C_{19}H_{19}N_5O_2$ % calculated C: 65.32, H: 5.48, N: 20.04, O: 9.16, % found C: 65.3, H: 5.5, N: 19.8, O: 9.5).

EXAMPLE 16

To a stirred mixture of 1.1 g of spiro[piperidine-4,10'-5'H,10'H-imidazo[1,2-a]indeno[1,2-e]pyrazine]-4'-one in 60 ml of dimethylformamide is added 1 ml of triethylamine and the stirring is continued for 30 minutes. 0.15 ml of methyl iodide is then added and the stirring is continued overnight at a temperature in the region of 20° C. 30 ml of water are added and the reaction mixture is filtered. The solid obtained is washed with acetone, then with a mixture of acetone and distilled water, and finally air-dried to give a beige product (470 mg). This crude product is purified on a column of silica, eluting with a dichloromethane/methanol mixture (80/20 by volume). 310 mg of product are obtained, which product is taken up in boiling ethyl acetate (50 ml). On crystallization after hot filtration, the filtrate gives 109 mg of 1-methylspiro[piperidine-4,10'-5'H,10'H-imidazo[1,2-a]indeno[1,2-e]pyrazine]-4'-one in the form of an off-white solid melting at about 232° C. with decomposition [NMR spectrum: (300 MHz; DMSO-$d_6$+$CD_3CO_2D$; δ in ppm): 1.60 (d, J=14 Hz, 1H: eq. CH); 2.77 (m, 1H: ax. CH); 3.01 (s, 3H: $NCH_3$); 3.50 (t, J=14 Hz, 1H: ax. NCH); 3.60 (m, 1H: eq. NCH); 7.40 (t, J=7 Hz, 1H: arom. CH); 7.53 (t, J=7 Hz, 1H: arom. CH); 7.73 (s, 1H: arom. CH); 8.00 (d, J=7 Hz, 1H: arom. CH); 8.22 (d, J=7 Hz, 1H: arom. CH); 8.40 (s, 1H: arom. CH)].

EXAMPLE 17

The process is performed as in Example 16 but starting with 746 mg of spiro[piperidine-4,10'-5'H,10'H-imidazo[1,2-a]indeno[1,2-e]pyrazine]-4'-one hydrobromide, 40 ml of dimethylformamide, 0.6 ml of triethylamine and 0.23 ml of benzyl chloride. The reaction mixture is concentrated on a rotavapor and the evaporation residue is triturated with a mixture of water and dichloromethane, and then filtered. The solid obtained is washed with distilled water, with ethyl ether, then again with distilled water and with ethyl ether. After drying at 35° C. under vacuum (1 mm Hg; 0.13 kPa), 440 mg of 1-benzylspiro[piperidine-4,10'-5'H,10'H-imidazo[1,2-a]indeno[1,2-e]pyrazine]-4'-one are obtained in the form of a light grey salt melting above 260° C. (analysis $C_{24}H_{22}N_4O$, 0.5 HBr, HCl % calculated C: 62.75, H: 5.16, Br: 8.70, Cl: 7.72, N: 12.20, O: 3.48, % found C: 62.8, H: 5.3, N: 12.3, O: 3.7).

EXAMPLE 18

The process is performed as in Example 16 but starting with 746 mg of spiro[piperidine-4,10'-5'H,10'H-imidazo[1,2-a]indeno[1,2-e]pyrazine]-4'-one hydrobromide, 40 ml of dimethylformamide, 0.6 ml of triethylamine and 0.26 ml of (2-chloroethyl)benzene, and by completing the stirring time of the reaction mixture by 6 hours of reflux. The reaction medium is filtered and the organic phase is evaporated on a rotavapor. The evaporation residue is triturated with a mixture of water and dichloromethane, and filtered. The solid obtained is washed with distilled water, then with ethyl ether (3×20 ml) and purified by chromatography on a column of silica, eluting with a dichloromethane/methanol mixture (95/5 by volume). The solid obtained (330 mg) is triturated in isopropyl ether, then in ethyl ether. After drying at 40° C. under vacuum (1 mm Hg; 0.13 kPa), 140 mg of 1-phenethylspiro[piperidine-4,10'-5'H,10'H-imidazo[1,2-a]indeno[1,2-e]pyrazine]-4'-one are obtained in the form of a beige-coloured salt melting above 260° C. (analysis $C_{25}H_{24}N_4O$, HBr, HCl % calculated C: 58.43, H: 5.10, Br: 15.55, Cl: 6.90, N: 10.90, O: 3.11, % found C: 58.1, H: 4.8, N: 11.0, O: 2.9).

EXAMPLE 19

The process is performed as in Example 16 but starting with 1 g of spiro[piperidine-4,10'-5'H,10'H-imidazo[1,2-a]indeno[1,2-e]pyrazine]-4'-one hydrobromide, 30 ml of dimethylformamide, 0.75 ml of triethylamine and 0.4 ml of 1-chloro-3-phenylpropane, and completing the stirring time of the reaction medium by 6 hours of reflux. The reaction mixture is concentrated on a rotavapor and the evaporation residue is triturated with isopropyl ether, and filtered. The brown solid obtained is purified by chromatography on a column of silica, eluting with a dichloromethane/methanol mixture (95/5 by volume). After trituration in ethyl ether, filtration and drying, 80 mg of 1-(3-phenylpropyl)spiro |piperidine-4,10'-5'H,10'H-imidazo|1,2-a|indeno|1,2-e| pyrazine|-4'-one are obtained in the form of a beige-coloured solid melting at about 215° C. with decomposition |NMR spectrum: (400 MHz; DMSO-d$_6$; δ in ppm) : 1.35 (2H, d, J=13 Hz, 2HCH piperidine), 1.90 (2H, m, CH$_2$), 2.58 (4H, m, 2HCH and NCH$_2$), 2.75 (4H, m, NCH$_2$ and 2 HCHN), 3.03 (2H, d, J=10 Hz, 2 HCHN), 7.22 (2H, t, J=7 Hz, CH phenyl), 7.33 (4H, m, 1 CH arom. and 3 CH phenyl), 7.45 (1H, t, J=7 Hz, CH arom.), 7.65 (1H, s, CH arom.), 7.95 (1H, d, J=7 Hz, CH arom.), 8.00 (1H, s, CH arom.), 8.03 (1H, d, J=7 Hz, CH arom.), 12.4 (1H, s, NH)|.

EXAMPLE 20

To a stirred suspension of 2.56 g of (10'RS)-spiro |piperidine-2,10'-5'H,10'H-imidazo|1,2-a|indeno|1,2-e| pyrazine|-4'-one in 40 ml of acetic acid are added 2.57 g of succinic anhydride and the stirring is continued for 48 hours at a temperature in the region of 20° C., and then at a temperature of 80° C. for 2 hours. The reaction mixture is concentrated on a rotavapor and 100 ml of absolute ethanol are added to the evaporation residue. The suspension obtained is filtered and the solid is washed with ethanol (2×3 ml) and dried at 60° C. under reduced pressure. A part (0.5 g) of the solid obtained is purified by chromatography on a column of silica, eluting with a dichloromethane/methanol/ 25% aqueous ammonia mixture (12/6/1 by volume). After trituration in isopropyl ether (5 ml), filtration and drying at 60° C. under vacuum (1 mm Hg; 0.13 kPa), 0.13 g of (10'RS)-4-oxo-4-{4'-oxo-4'5'-dihydrospiro|piperidine-2, 10'-10'H-imidazo|1,2-a|indeno|1,2-e|pyrazin-1-yl|}butyric acid is obtained in the form of a cream-coloured solid melting at about 220° C. with decomposition (analysis C$_{21}$H$_{20}$N$_4$O$_4$ % calculated C: 64.28, H: 5.14, N: 14.28, O: 16.31, % found C: 63.9, H: 4.7).

EXAMPLE 21

To a stirred solution of 0.89 g of (10'RS)-spiro|piperidine-2,10'-5'H,10'H-imidazo|1,2-a|indeno|1,2-e|pyrazine|-4'-one in 1.15 ml of formic acid are added 2.3 ml of 37% formaldehyde and the stirring is continued for 2 hours at a temperature in the region of 20° C., then for 45 minutes at a temperature of between 30° and 40° C. The reaction mixture is concentrated on a rotavapor, 10 ml of absolute ethanol are added to the residue and the solution is filtered. The filtrate is evaporated on a rotavapor and the evaporation residue is triturated with 10 ml of hot distilled water and filtered. The solid obtained is washed with distilled water (3×5 ml) and then with acetone (2×5 ml). After drying at 60° C. under vacuum (1 mm Hg; 0.13 kPa), 0.25 g of (10'RS) -1-methylspiro|piperidine-2,10'-5'H,10'H-imidazo|1,2-a| indeno|1,2-e|pyrazine|-4'-one is obtained in the form of a cream-coloured solid melting at about 240° C. with decomposition (analysis C$_{18}$H$_{18}$N$_4$O % calculated C: 70.57, H: 5.92, N: 18.29, O: 5.22, % found C: 70.7, H: 5.5, N: 18.2).

EXAMPLE 22

The process is performed as in Example 3 but starting with 3.9 g of 10-acetylamino-5H,10H-imidazo|1,2-a|indeno |1,2-e|pyrazine|-4-one, 43 ml of dimethyl sulphoxide, 1.7 g of 80% sodium hydride and 1.5 ml of 1-bromo-3-chloropropane. After hydrolysis, the reaction medium is subjected to extractions with ethyl acetate (4×300 ml) and the aqueous phase is evaporated on a rotavapor. The gummy residue is triturated with 30 ml of distilled water, filtered, washed with distilled water (5 ml) and air-dried to give a greenish-grey solid (2.3 g). 160 ml of distilled water are added to a part (1.3 g) of this product and the mixture is heated at reflux for 5 minutes, then filtered while hot. The filtrate is left in an ice-water bath for one hour and the precipitate formed is filtered off, washed with distilled water (2×5 ml) and dried at 60° C. under vacuum (1 mm Hg; 0.13 kPa). 0.52 g of (10'RS)-1-acetylspiro|pyrrolidine-2,10'-5'H, 10'H-imidazo|1,2-a|indeno|1,2-e|pyrazine|-4'-one is obtained in the form of a light grey solid melting at 270° C. with decomposition (analysis C$_{18}$H$_{16}$N$_4$O$_2$ % calculated C: 67.49; H: 5.03, N: 17.49, O: 9.99, % found C: 67.3, H: 5.3, N: 17.6).

10-Acetylamino-5H,10H-imidazo|1,2-a|indeno|1,2-e| pyrazine|-4-one may be obtained as described in patent FR 2,707,643.

EXAMPLE 23

To a stirred solution of 1.1 g of spiro|pyrrolidine-2,10'- 5'H,10'H-imidazo|1,2-a|indeno|1,2-e|pyrazine|-4'-one in 45 ml of dimethylformamide is added 0.56 ml of triethylamine followed, over 5 minutes, by a solution of 0.89 g of N-phthaloylglycyl chloride in 10 ml of dimethylformamide. The stirring is continued for 16 hours at a temperature in the region of 20° C. The reaction medium is evaporated on a rotavapor and the residue is triturated with distilled water (3×40 ml), filtered and air-dried. A part (0.31 g) of the crude product obtained (1.54 g) is triturated in ethyl acetate (4×50 ml), then in isopropyl ether (4×40 ml) and dried at 60° C. under vacuum (1 mm Hg; 0.13 kPa). 0.28 g of (10'RS)-1- phthalimidoacetylspiro|pyrrolidine-2,10'-5'H,10'H-imidazo |1,2-a|indeno|1,2-e|pyrazine|-4'-one is obtained in the form of a light brown solid decomposing at about 350° C. (analysis C$_{26}$H$_{19}$N$_5$O$_4$ % calculated C: 67.09, H: 4.11, N: 15.05, O: 13.75, % found C: 67.1, H: 4.1, N: 15.0).

EXAMPLE 24

To a stirred suspension of 4.65 g of (10'RS)-1- phthalimidoacetylspiro|pyrrolidine-2,10'-5'H,10'H-imidazo |1,2-a|indeno|1,2-e|pyrazine|-4'-one in 10 ml of methanol are added 2 ml of hydrazine hydrate and the mixture is heated at reflux for 16 hours. After cooling to a temperature in the region of 20° C., the suspension obtained is filtered and the solid is washed with methanol (3×30 ml). The methanolic filtrate is evaporated on a rotavapor and the evaporation residue is purified by chromatography on a column of silica, eluting with a dichloromethane/ methanol/ 25% aqueous ammonia mixture (70/30/3 by volume). After washing with ethyl acetate (4×20 ml) and then with isopropyl ether (4×30 ml), 1.7 g of (10'RS)-1-glycylspiro |pyrrolidine-2,10'-5'H,10'H-imidazo|1,2-a|indeno|1,2-e| pyrazine|-4'-one are obtained in the form of a cream-yellow solid decomposing at about 290° C. (analysis C$_{18}$H$_{17}$N$_5$O$_2$ % calculated C: 64.47, H: 5.11, N: 20.88, O: 9.54, % found C: 64.4, H: 4.7, N: 21.0).

EXAMPLE 25

To a stirred solution of 670 mg of (10'RS)-1-glycylspiro |pyrrolidine-2,10'-5'H,10'H-imidazo|1,2-a|indeno|1,2-e| pyrazine|-4'-one in 35 ml of dimethylformamide is added 0.13 ml of methyl isocyanate and the stirring is continued for 2 hours at a temperature in the region of 20° C. The reaction mixture is evaporated on a rotavapor and the evaporation residue is triturated with isopropyl ether (3×5 ml). After filtration and drying at 60° C. under vacuum (1 mm Hg; 0.13 kPa), 770 mg of (10'RS)-1-[(3-methylureido)-acetyl]spiro |pyrrolidine-2,10'-5'H,10'H-imidazo| 1,2-a|indeno| 1,2-e| pyrazine|-4'-one are obtained in the form of a cream-coloured solid decomposing at about 290° C. (analysis $C_{20}H_{20}N_6O_3$ % calculated C: 61.22, H: 5.14, N: 21.42, O: 12.23, % found C: 60.3, H: 5.2, N: 21.4).

EXAMPLE 26

The process is performed as in Example 25 but starting with 1 g of (10'RS)-spiro|pyrrolidine-2,10'-5'H,10'H-imidazo| 1,2-a|indeno| 1,2-e|pyrazine|-4'-one, 50 ml of dimethylformamide and 0.23 ml of methyl isocyanate. After evaporation of the reaction mixture, the residue is triturated in 50 ml of acetone, filtered, washed with acetone (3×5 ml) and dried at 60° C. under vacuum (1 mm Hg; 0.13 kPa). 1.15 g of (10'RS)-1-(methylcarbamoyl)spiro[pyrrolidine-2,10'-5'H,10'H-imidazo| 1,2-a|indeno| 1,2-e|pyrazine|-4'-one are obtained in the form of a cream-coloured solid decomposing at about 270° C. (analysis $C_{18}H_{17}N_5O_2$ % calculated C: 64.47, H: 5.11, N: 20.88, O: 9.54, % found C: 64.4, H: 4.9, N: 20.8).

EXAMPLE 27

The process is performed as in Example 26 but starting with 1 g of (10'RS)-spiro|pyrrolidine-2,10'-5'H,10'H-imidazo| 1,2-a|indeno| 1,2-e|pyrazine|-4'-one, 50 ml of dimethylformamide and 0.44 ml of phenyl isocyanate. 1.1 g of (10'RS)-1-(phenylcarbamoyl)spiro[pyrrolidine-2,10'-5'H,10'H-imidazo| 1,2-a|indeno| 1,2-e|pyrazine|-4'-one are obtained in the form of a white solid decomposing at about 280° C. (analysis $C_{23}H_{19}N_5O_2$ % calculated C: 69.51, H: 4.82, N: 17.62, O: 8.05, % found C: 69.5, H: 4.9, N: 17.3, O: 7.7).

EXAMPLE 28

The process is performed as in Example 26 but starting with 1 g of (10'RS)-spiro|pyrrolidine-2,10'-5'H,10'H-imidazo| 1,2-a|indeno| 1,2-e|pyrazine|-4'-one, 50 ml of dimethylformamide and 0.49 ml of benzyl isocyanate. 1.3 g of (10'RS)-1-(benzylcarbamoyl)spiro[pyrrolidine-2,10'-5'H,10'H-imidazo| 1,2-a|indeno| 1,2-e|pyrazine|-4'-one are obtained in the form of a white solid melting at 240° C. then decomposing (analysis $C_{24}H_{21}N_5O_2$ % calculated C: 70.06, H: 5.14, N: 17.02, O: 7.78, % found C: 69.8, H: 5.4, N: 17.0).

EXAMPLE 29

The process is performed as in Example 6 but starting with 0.85 g of (10'RS)-8'-fluorospiro[pyrrolidine-2,10'-5'H,10'H-imidazo| 1,2-a|indeno| 1,2-e|pyrazine|-4'-one, 2.13 ml of 37% formaldehyde and 1.1 ml of formic acid. After evaporation of the reaction mixture, the residue is chromatographed on a column of silica, eluting with a dichloromethane/methanol mixture (90/10 by volume). 150 ml of methanol are added to the yellow solid obtained (0.61 g); the mixture is maintained at reflux for 10 minutes and filtered while hot. The filtrate is evaporated on a rotavapor and the evaporation residue is triturated with 30 ml of ethyl ether, filtered and dried at 60° C. under vacuum (1 mm Hg; 0.13 kPa). 0.41 g of (10'RS)-1-methyl-8'-fluorospiro |pyrrolidine-2,10'-5'H,10'H-imidazo| 1,2-a|indeno| 1,2-e| pyrazine|-4'-one is obtained in the form of a white solid melting at about 310° C. with decomposition (analysis $C_{17}H_{15}FN_4O$ % calculated C: 65.80, H: 4.87, F: 6.12, N: 18.05, O: 5.16, % found C: 65.9, H: 4.6, F: 6.0, N: 17.8).

(10'RS)-8'-Fluorospiro|pyrrolidine-2,10'-5'H,10'H-imidazo| 1,2-a|indeno| 1,2-e|pyrazine|-4'-one may be prepared in the following way: the process is performed as in Example 3 but starting with 2.37 g of 10-tert-butoxycarbonylamino-8-fluoro-5H,10H-imidazo| 1,2-a| indeno| 1,2-e|pyrazin-4-one, 22.5 ml of dimethyl sulphoxide, 0.81 g of 80% sodium hydride and 0.72 ml of 1-bromo-3-chloropropane. 2.2 g of (10'RS)-1-tert-butoxycarbonylamino-8'-fluorospiro|pyrrolidine-2,10'-5'H,10'H-imidazo| 1,2-a|indeno| 1,2-e|pyrazine|-4'-one are obtained as intermediate, in the form of a white solid melting above 260° C. (Rf=0.57, thin layer chromatography on silica gel, eluent: chloroform/methanol/28% aqueous ammonia (12/3/0.5 by volume)). Deprotection of the NH was carried out on 0.88 g of (10'RS)-1-tert-butoxycarbonylamino-8'-fluorospiro|pyrrolidine-2,10'-5'H,10'H-imidazo| 1,2-a| indeno| 1,2-e|pyrazine|-4'-one using 9 ml of trifluoroacetic acid. 0.45 g of (10'RS)-8'-fluorospiro|pyrrolidine-2,10'-5'H,10'H-imidazo| 1,2-a|indeno| 1,2-e|pyrazine|-4'-one is obtained in the form of a beige-coloured solid decomposing at about 260° C. (Rf=0.50, thin layer chromatography on silica gel, eluent: chloroform/methanol/28% aqueous ammonia (12/3/0.5 by volume)).

10-tert-Butoxycarbonylamino-8-fluoro-5H,10H-imidazo |1,2-a|indeno| 1,2-e|pyrazin-4-one may be prepared in the following way: the process is performed as in Example 3 but starting with 0.44 g of 10-amino-8-fluoro-5H,10H-imidazo | 1,2-a|indeno| 1,2-e|pyrazin-4-one, 5.5 ml of dimethylformamide, 0.26 ml of triethylamine and 0.5 g of di-tert-butyl dicarbonate. 0.16 g of 10-tert-butoxycarbonylamino-8-fluoro-5H,10H-imidazo| 1,2-a| indeno|1,2-e|pyrazin-4-one is obtained in the form of a grey-white solid melting above 260° C. (Rf=0.53, thin layer chromatography on silica gel, eluent: chloroform/methanol/ 28% aqueous ammonia (12/3/0.5 by volume)).

10-Amino-8-fluoro-5H,10H-imidazo| 1,2-a|indeno|1,2-e| pyrazin-4-one may be obtained as described in patent FR 2,707,643.

EXAMPLE 30

A stirred solution of 778 mg of (10'RS)-spiro|pyrrolidine-2,10'-5'H,10'H-imidazo| 1,2-a|indeno| 1,2-e|pyrazine|-4'-one in 5 ml of acetic acid is heated to a temperature in the region of 45° C., and 510 mg of sodium borohydride are added over 1 hour. The stirring is maintained at this temperature for 16 hours. The reaction medium is then poured into 50 ml of distilled water and left to stand for 1 hour at a temperature in the region of 20° C. The precipitate formed is filtered off, washed with distilled water (3×30 ml) and air-dried. The crude product is purified by chromatography on a column of silica, eluting with ethyl acetate. After drying at 60° C. under vacuum (1 mm Hg; 0.13 kPa), 230 mg of (10'RS)-1-ethylspiro|pyrrolidine-2,10'-5'H,10'H-imidazo| 1,2-a|indeno| 1,2-e|pyrazine|-4'-one are obtained in the form of a white solid melting at 228° C. (analysis $C_{18}H_{18}N_4O$ % calculated C: 70.57, H: 5.92, N: 18.29, O: 5.22, % found C: 70.6, H: 6.1, N: 18.3).

EXAMPLE 31

The process is performed as in Example 30 but starting with 778 mg of (10'RS)-spiro|pyrrolidine-2,10'-5'H,10'H-imidazo| 1,2-a|indeno| 1,2-e|pyrazine|-4'-one, 6.5 ml of propionic acid and 510 mg of sodium borohydride. The crude product (740 mg) is purified by crystallization from 25 ml of ethyl acetate. 430 mg of (10'RS)-1-propylspiro|pyrrolidine-2,10'-5'H,10'H-imidazo|1,2-a|indeno|1,2-e|pyrazine|-4'-one are obtained in the form of a light yellow solid melting at 248° C. (analysis $C_{19}H_{20}N_4O$ % calculated C: 71.23, H: 6.29, N: 17.49, O: 4.99, % found C: 71.5, H: 6.4, N: 17.4, O: 5.2).

EXAMPLE 32

To a stirred suspension of 1 g of (10'RS)-spiro|pyrrolidine-2,10'-5'H,10'H-imidazo|1,2-a|indeno|1,2-e|pyrazine|-4'-one in 50 ml of absolute ethanol is added 0.45 g of potassium hydroxide pellets. 1 ml of benzyl bromide is added to the orange-yellow solution obtained and the mixture is stirred overnight at a temperature in the region of 20° C. The reaction mixture is evaporated on a rotavapor and the evaporation residue is triturated in ethyl acetate (3×40 ml) and filtered. The solid is treated with acetic acid and concentrated on a rotavapor. The foam obtained is purified on a column of silica, eluting with a mixture of ethyl acetate and methanol (90/10 by volume). 73 mg of (10'RS)-1-benzylspiro|pyrrolidine-2,10'-5'H,10'H-imidazo|1,2-a|indeno|1,2-e|pyrazine|-4'-one are obtained in the form of a beige-coloured solid [NMR spectrum: (300 MHz; DMSO-$d_6$; δ in ppm): 2.05 and 2.65 (m, 1H each: $CH_2$); 2.35 (m, 2H: $CH_2$); 3.12 and 3.40 (m, 1H each: $NCH_2$); 3.15 and 3.23 (m, 1H each: $NCH_2Ph$); 6.95 (t, J=7 Hz, 2H: phenyl CH); 7.02 (m, 3H: phenyl CH); 7.40 (t, J=7 Hz, 1H: arom. CH); 7.47 (t, J=7 Hz, 1H: arom. CH); 7.60 (d, J=7 Hz, 1H: arom. CH); 7.65 (s, 1H: arom. CH); 7.89 (d, J=7 Hz, 1H: arom. CH); 8.10 (s, 1H: arom. CH); 12.3 (s, 1H: NH).

EXAMPLE 33

The process is performed as in Example 22 but starting with 3.9 g of 10-acetylamino-5H,10H-imidazo|1,2-a|indeno|1,2-e|pyrazine|-4-one, 66 ml of dimethyl sulphoxide, 1.7 g of 80% sodium hydride and 1.85 ml of methyl 3-bromopropionate. After hydrolysis, the reaction medium is filtered and the solid is washed with distilled water (2×30 ml) and air-dried. The crude product is chromatographed on a column of silica, eluting with a chloroform/methanol/28% aqueous ammonia mixture (12/3/0.5 by volume). An orange-yellow solid is obtained (0.31 g), to which are added 20 ml of ethyl acetate and 3 ml of propanol. The mixture is heated at reflux for 10 minutes and cooled in an ice-water bath. After filtration, washing with ethyl acetate (2×5 ml), then with ethyl ether (5 ml) and drying at 60° C. under vacuum (1 mm Hg; 0.13 kPa), 0.17 g of (10'RS)-spiro|pyrrolidine-2,10'-5'H,10'H-imidazo|1,2-a|indeno|1,2-e|pyrazine|-4',5-dione is obtained in the form of a pink-beige solid decomposing at about 350° C. (analysis $C_{16}H_{12}N_4O_2$ % calculated C: 65.75, H: 4.14, N: 19.17, O: 10.95, % found C: 65.7, H: 3.8, N: 19.0).

The medicinal products according to the invention consist of a compound of formula (I) or a salt of such a compound, in the pure state or in the form of a composition in which it is combined with any other pharmaceutically compatible product, which may be inert or physiologically active. The medicinal products according to the invention may be employed orally, parenterally, rectally or topically.

As solid compositions for oral administration, tablets, pills, powders (gelatin capsules or wafer capsules) or granules may be used. In these compositions, the active principle according to the invention is mixed with one or more inert diluents, such as starch, cellulose, sucrose, lactose or silica, under a stream of argon. These compositions may also contain substances other than diluents, for example one or more lubricating agents such as magnesium stearate or talc, a dye, a coating agent (dragees) or a varnish.

As liquid compositions for oral administration, pharmaceutically acceptable solutions, suspensions, emulsions, syrups and elixirs containing inert diluents such as water, ethanol, glycerol, vegetable oils or paraffin oil may be used. These compositions may contain substances other than diluents, for example wetting, sweetening, thickening, flavouring or stabilizing products.

The sterile compositions for parenteral administration may preferably be aqueous or non-aqueous solutions, suspensions or emulsions. Water, propylene glycol, a polyethylene glycol, vegetable oils, in particular olive oil, injectable organic esters, for example ethyl oleate or other suitable organic solvents may be employed as solvent or vehicle. These compositions may also contain adjuvants, in particular wetting, tonicity, emulsifying, dispersing and stabilizing agents. The sterilization may be effected in several ways, for example by aseptic filtration, by incorporating sterilizing agents into the composition, by irradiation or by heating. They may also be prepared in the form of sterile solid compositions which may be dissolved at the time of use in sterile water or any other injectable sterile medium.

The compositions for rectal administration are suppositories or rectal capsules which contain, besides the active product, excipients such as cocoa butter, semi-synthetic glycerides or polyethylene glycols.

The compositions for topical administration may for example be creams, lotions, eyedrops, mouthwashes, nasal drops or aerosols.

In human therapy, the compounds according to the invention are particularly useful for the treatment and/or prevention of the conditions which require the administration of an antagonist of the AMPA receptor or of an antagonist of the NMDA receptor. These compounds are in particular useful for treating or preventing all ischemias and in particular cerebral ischemia, the effects of anoxia, for treating or preventing the development of neurodegenerative diseases, Huntington's chorea, Alzheimer's disease, amyotrophic lateral sclerosis, olivopontocerebellar atrophy and Parkinson's disease. These compounds may also be used with regard to epileptogenic and/or convulsive symptoms, for the treatment of cerebral or spinal trauma, trauma associated with degeneration of the middle ear or of the retina, of anxiety, depression, schizophrenia, Tourette's syndrome, hepatic encephalopathy, as analgesics, as anti-inflammatory agents, as anti-anorexic agents, as anti-migraine and anti-emetic agents and for the treatment of poisoning by neurotoxins or other substances which are agonists of the NMDA receptor, as well as neurological problems associated with viral diseases such as AIDS, rabies, measles and tetanus. These compounds are also useful for the prevention of the symptoms of withdrawal from drugs and alcohol, and for inhibiting the addiction to and dependency on opiates. They may also be used in the treatment of deficiencies associated with mitochondrial anomalies such as mitochondrial myopathy, Leber's syndrome, Wernicke's encephalopathy, Rett's syndrome, homocysteinaemia, hyperprolinaemia, hydroxybutyric aminoaciduria, lead encephalopathy and sulphite oxidase deficiency.

The doses depend upon the effect sought, the duration of the treatment and the administration route used; they are generally between 10 mg and 100 mg per day via the oral route for an adult with unit doses ranging from 5 mg to 50 mg of active substance.

Generally speaking, the doctor will determine the appropriate dosage depending on the age, weight and all the other factors which are specific to the subject to be treated.

The examples which follow illustrate compositions according to the invention:

EXAMPLE A

Gelatin capsules containing a 50 mg dose of active product and having the following composition are prepared according to the usual technique:

Compound of formula (I) . . . 50 mg

Cellulose . . . 18 mg

Lactose . . . 55 mg

Colloidal silica . . . 1 mg

Sodium carboxymethyl starch . . . 10 mg

Talc . . . 10 mg

Magnesium stearate . . . 1 mg

EXAMPLE B

Tablets containing a 50 mg dose of active product and having the following composition are prepared according to the usual technique:

Compound of formula (I) . . . 50 mg

Lactose . . . 104 mg

Cellulose . . . 40 mg

Polyvidone . . . 10 mg

Sodium carboxymethyl starch . . . 22 mg

Talc . . . 10 mg

Magnesium stearate . . . 2 mg

Colloidal silica . . . 2 mg

Mixture of hydroxymethyl cellulose, glycerol and titanium oxide (72/3.5/24.5) qs 1 finished film-coated tablet containing . . . 245 mg

EXAMPLE C

An injectable solution containing 10 mg of active product and having the following composition is prepared:

Compound of formula (i) . . . 10 mg

Benzoic acid . . . 80 mg

Benzyl alcohol . . . 0.06 ml

Sodium benzoate . . . 80 mg

95% ethanol . . . 0.4 ml

Sodium hydroxide . . . 24 mg

Propylene glycol . . . 1.6 ml

Water . . . q.s. 4 ml

We claim:

1. A compound of formula (I):

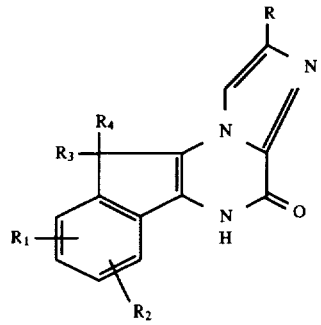

in which

R represents a hydrogen atom or a carboxyl, alkoxycarbonyl or carboxamido radical;

$R_1$ and $R_2$, which may be identical or different, represent hydrogen or halogen atoms or alkyl, alkoxy, amino, —N=CH—N(alk)alk', nitro, cyano, phenyl, imidazolyl, $SO_3H$, hydroxyl, polyfluoroalkoxy, carboxyl, alkoxycarbonyl, —NH—CO—$NR_5R_6$, —N(alk)—CO—$NR_5R_6$, —N(alk—Ar)—CO—$NR_5R_6$, —NH—CS—$NR_5R_6$, —N(alk)—CS—$NR_5R_6$, —NH—CO—$R_5$, —NH—CS—$R_7$, —NH—C(=$NR_9$)—$NR_8R_6$, —N(alk)—C(=$NR_9$)—$NR_8R_6$, —CO—$NR_8R_6$, —NH—$SO_2$—$NR_8R_6$, —N(alk)—$SO_2$—$NR_8R_6$, —NH—$SO_2$—$CF_3$, —NH—$SO_2$—alk, —NH—$SO_2$—Ar, —$NR_8R_{10}$, —$S(O)_m$—alk—Ar or —$SO_2$—$NR_8R_6$ radicals, or a 2-oxo-1-imidazolidinyl radical in which the 3-position is optionally substituted with an alkyl radical, or a 2-oxoperhydro-1-pyrimidinyl radical in which the 3-position is optionally substituted with an alkyl radical;

$R_3$ and $R_4$, together with the carbon atom to which they are attached, form (a) a 2- or 3-pyrrolidine ring, a 2- or 4-piperidine ring or a 2-azacycloheptane ring, said rings optionally being substituted on the nitrogen thereof with an alkyl, —CHO, —$COOR_{11}$, —CO—alk—$COOR_6$, —CO—alk—$NR_6R_{12}$, —CO—alk—$CONR_6R_8$, —CO—$COOR_6$, —CO—$CH_2$—O—$CH_2$—$COOR_6$, —CO—$CH_2$—S—$CH_2$—$COOR_6$, —CO—CH=CH—$COOR_6$, CO—alk, —CO—Ar", —CO—alk—Ar", —CO—NH—Ar", —CO—NH—alk—Ar", —CO—Het, —CO—alk—Het, —CO—NH—Het, —CO—NH—alk—Het, —CO—$NH_2$, —CO—NH—alk, —CO—N(alk)alk', —CS—$NH_2$, —CS—NH—alk, —CS—NH—Ar", —CS—NH—Het, —alk—Het, —alk—$NR_6R_8$, —alk—$COOR_6$, —alk—CO—$NR_6R_8$, —alk—Ar", -$SO_2$—alk or —$SO_2$—Ar radical, or a —CO-cycloalkyl radical in which the cycloalkyl is optionally substituted in the 2-position with a carboxyl radical, or (b) a 2-pyrrolidin-5-one ring;

$R_5$ represents a hydrogen atom, a straight or branched alkyl chain having from 1 to 9 carbon atoms, an —alk—$COOR_8$, —alk—Het or —alk—$NR_6R_8$ radical, a phenylalkyl radical in which the phenyl ring is optionally substituted with one or more substituents selected from halogen and alkyl, alkoxy, nitro, amino, hydroxyl, —alk—$NH_2$, carboxyl, alkoxycarbonyl, cyano and —alk—$COOR_8$ radicals, a phenyl radical which is optionally substituted with one or more substituents selected from halogen atoms and alkyl, alkoxy, nitro, amino, hydroxyl, —alk—$NH_2$, carboxyl, alkoxycarbonyl, cyano and —alk—COOR$_8$ radicals, or a —Het radical;

R$_6$ represents a hydrogen atom or an alkyl radical;

R$_7$ represents an alkyl or phenyl radical;

R$_8$ represents a hydrogen atom or an alkyl radical;

R$_9$ represents a hydrogen atom or an alkyl radical;

R$_{10}$ represents an alkyl, Het or alkoxycarbonyl radical;

R$_{11}$ represents an alkyl or phenylalkyl radical;

R$_{12}$ represents a hydrogen atom or an alkyl or —CO—NH—alk radical;

alk represents an alkyl or alkylene radical;

alk' represents an alkyl radical;

m is equal to 0, 1 or 2;

Ar represents a phenyl radical;

Ar" is an unsubstituted phenyl radical or a phenyl radical substituted with one or more substituents selected from halogen and alkyl, alkoxy, nitro, amino, hydroxyl, cyano, —alk—NH$_2$, COOR$_6$ and —alk—COOR$_6$ radicals;

Het represents (a) a saturated or unsaturated mono- or polycyclic heterocycle containing 1 to 9 carbon atoms and one or more heteroatoms, said heteroatoms being selected from O, S and N, said heterocycle being optionally substituted with one or more alkyl, phenyl, carboxyl or phenylalkyl radicals, or (b) a phthalimido radical;

it being understood that, except where otherwise mentioned, the alkyl, alkylene and alkoxy radicals and portions of radicals contain 1 to 6 carbon atoms and are in a straight or branched chain, and the cycloalkyl radicals contain 3 to 6 carbon atoms;

an enantiomer or diastereoisomer of said compound of formula (I) for which R$_3$ and R$_4$, together with the carbon atom to which they are attached, form a 2- or 3-pyrrolidine ring, a 2-piperidine ring, a 2-pyrrolidin-5-one ring or a 2-azacycloheptane ring, a cis or trans isomer of said compound of formula (I) containing a radical —CO—CH=CH—COOR$_6$, or a salt of said compound of formula (I).

2. A compound of formula (I) according to claim 1, wherein Het is selected from a pyrrolyl ring, pyridyl ring, a pyrimidinyl ring, an imidazolyl ring, a thiazolyl ring, an oxazolinyl ring, a thiazolinyl ring, a pyrazinyl ring, a tetrazolyl ring, and a triazolyl ring, or a salt thereof, said rings being optionally substituted with one or more alkyl, phenyl, carboxyl or phenylalkyl radicals.

3. A compound of formula (I) according to claim 1, wherein R represents a hydrogen atom or a carboxyl, alkoxycarbonyl or carboxamido radical; R$_1$ and R$_2$are hydrogen or halogen atoms; and R$_3$ and R$_4$, together with the carbon atom to which they are attached, form a 2- or 3-pyrrolidine ring or a 2- or 4-piperidine ring, said rings optionally being substituted on the nitrogen thereof with an alkyl, —COOR$_{11}$, —CO—alk—Ar", —CO—NH—alk, —CO—NH—Ar", —CO—alk, —alk—Ar", —CO—alk—NR$_6$R$_{12}$ or —CO—alk—COOR$_6$ radical, or a 2-pyrrolidin-5-one ring, or a salt thereof.

4. A compound, said compound being:

(10'RS)-spiro|pyrrolidine-3,10'-5'H,10'H-imidazo-|1,2-a|indeno|1,2-e|pyrazine|-4'-one, (10'RS)-spiro|piperidine-2,10'-5'H,10'H-imidazo-|1,2-a|indeno|1,2-e|pyrazine|-4'-one, (10'RS)-spiro|pyrrolidine-2,10'-5'H,10'H-imidazo-|1,2-a|indeno|1,2-e|pyrazine|-4'-one, (10'RS)-1-methylspiro|pyrrolidine-2,10'-5'H, 10'H-imidazo|1,2-a|indeno|1,2-e|pyrazine|-4'-one, (+)-1-methylspiro|pyrrolidine-2,10'-5'H,10'H-imidazo|1,2-a|indeno|1,2-e|pyrazine|-4'-one, (−)-1-methylspiro|pyrrolidine-2,10'-5'H,10'H-imidazo|1,2-a|indeno|1,2-e|pyrazine|-4'-one, (10'RS)-4-oxo-4-{4'-oxo-4',5'-dihydrospiro-|pyrrolidine-2,10'-10'H-imidazo|1,2-a|indeno|1,2-e|pyrazin-1-yl|}butyric acid, spiro|piperidine-4,10'-5'H,10'H-imidazo|1,2-a|indeno|1,2-e|pyrazine|-4'-one, 4-oxo-4-{4'-oxo-4',5'-dihydrospiro|piperidine-4,10'-10'H-imidazo|1,2-a|indeno|1,2-e|pyrazin-1-yl|}butyric acid, 1-phenylacetylspiro|piperidine-4,10'-5'H,10'H-imidazo|1,2-a|indeno|1,2-e|pyrazine|-4'-one, 1-(methylcarbamoyl)spiro|piperidine-4,10'-5'H,10'H-imidazo|1,2-a|indeno|1,2-e|pyrazine|-4'-one, 1-methylspiro|piperidine-4,10'-5'H,10'H-imidazo-|1,2-a|indeno|1,2-e|pyrazine|-4'-one, 1-benzylspiro|piperidine-4,10'-5'H,10'H-imidazo-|1,2-a|indeno|1,2-e|pyrazine|-4'-one, 1-phenethylspiro|piperidine-4,10'-5'H,10'H-imidazo-|1,2-a|indeno|1,2-e|pyrazine|-4'-one, (10'RS)-1-acetylspiro|pyrrolidine-2,10'-5'H,10'H-imidazo|1,2-a|indeno|1,2-e|pyrazine|-4'-one, (10'RS)-1-|(3-methylureido)acetyl|spiro-|pyrrolidine-2,10'-5'H,10'H-imidazo|1,2-a|indeno|1,2-e|pyrazine|-4'-one, (10'RS)-1-(phenylcarbamoyl)spiro|pyrrolidine-2,10'-5'H,10'H-imidazo|1,2-a|indeno|1,2-e|pyrazine|-4'-one, (10'RS)-1-methyl-8'-fluorospiro|pyrroldine-2,10'-5'H,10'H-imidazo|1,2-a|indeno|1,2-e|pyrazine|-4'-one, (10'RS)-1-ethylspiro|pyrrolidine-2,10'-5'H,10'H-imidazo |1,2-a|indeno|1,2-e|pyrazine|-4'-one, (10'RS)-1-propylspiro|pyrrolidine-2,10'-5'H,10'H-imidazo|1,2-a|indeno|1,2-e|pyrazine|-4'-one, (10'RS)-4-oxo-4-{4'-oxo-4',5'-dihydrospiro-|pyrrolidine-2,10'-10'H-imidazo|1,2-a|indeno|1,2-e|pyrazin-1-yl|}-butyric, or a salt of one of said compounds.

5. A process for preparing a compound of formula (I) according to claim 1, wherein R$_3$ and R$_4$, together with the carbon atom to which they are attached, form a 2-pyrrolidine ring, a 2-piperidine ring or a 2-azacycloheptane ring, said process comprising reacting a derivative of formula (II):

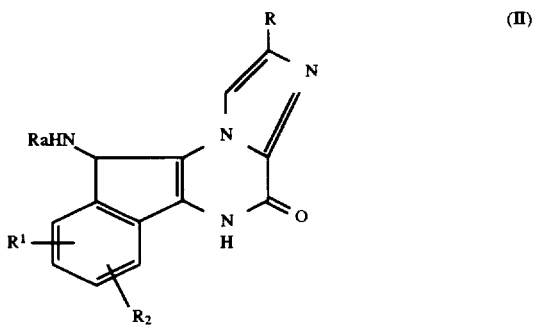

in which Ra represents a protecting group for the amine function and R, R$_1$ and R$_2$ have the same meanings as recited in claim 1, with a derivative of formula (III):

in which Hal and Hal', which may be identical or different, are halogen atoms and p is equal to 3, 4 or 5; deprotecting the NH thereof; isolating the product of said deprotection; and optionally converting said isolated product into a salt.

6. A process for preparing a compound of formula (I) according to claim 1, wherein $R_3$ and $R_4$, together with the carbon atom to which they are attached, form a 3-pyrrolidine ring, said process comprising reacting N-n-butoxymethyl-N-trimethylsilylmethylbenzylamine with a derivative of formula (XI):

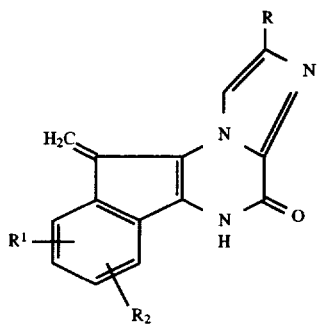

(XI)

in which R, $R_1$ and $R_2$ have the same meanings as recited in claim 1; debenzylating the NH thereof; isolating the product of said debenzylation; and optionally converting said isolated product into a salt.

7. A process for preparing a compound of formula (I) according to claim 1, wherein $R_3$ and $R_4$, together with the nitrogen atom to which they are attached, form a 4-piperidine ring, said process comprising reacting N,N-bis(2-chloroethyl)-p-toluenesulphonamide with a derivative of formula (V):

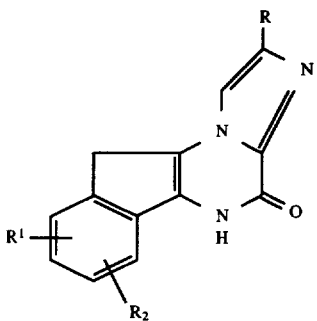

(V)

in which R; $R_1$ and $R_2$ have the same meanings as recited in claim 1; hydrolysing the sulphonamide function thereof; isolating the product of said hydrolysation; and optionally converting said isolated product into a salt.

8. A process for preparing a compound of formula (I) according to claim 1, wherein $R_3$ and $R_4$, together with the carbon atom to which they are attached, form a 2-pyrrolidin-5-one ring, said process comprising reacting a derivative of formula (II):

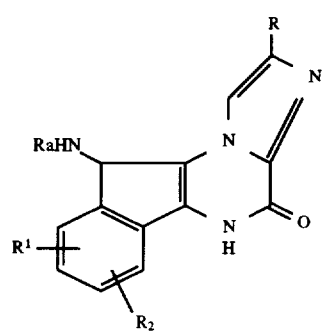

(II)

in which Ra represents an acetyl radical and R, $R_1$ and $R_2$ have the same meanings as recited in claim 1 with methyl 3-bromopropionate; isolating the product of said reaction; and optionally converting said isolated product into a salt.

9. A process for preparing a compound of formula (I) according to claim 1, for which $R_3$ and $R_4$, together with the carbon atom to which they are attached, form a 2- or 3-pyrrolidine ring, a 2- or 4-piperidine ring or a 2-azacycloheptane ring in which the nitrogen atom is substituted with an alkyl radical having one carbon atom, said process comprising reacting formaldehyde and formic acid with a compound of formula (I) in which $R_3$ and $R_4$, together with the carbon atom to which they are attached, form a 2- or 3-pyrrolidine ring, a 2- or 4-piperidine ring or a 2-azacycloheptane ring; isolating the product of said reaction; and optionally converting said isolated product into a salt.

10. A process for preparing a compound of formula (I) according to claim 1, wherein $R_3$ and $R_4$, together with the carbon atom to which they are attached, form a 2- or 3-pyrrolidine ring, a 2- or 4-piperidine ring or a 2-azacycloheptane ring in which the nitrogen atom is substituted with an alkyl radical having 2 to 6 carbon atoms, said process comprising reacting, in the presence of sodium borohydride, an acid alk—COOH in which alk represents an alkyl radical having 1 to 5 carbon atoms with a compound of formula (I) in which $R_3$ and $R_4$, together with the carbon atom to which they are attached, form a 2- or 3-pyrrolidine ring, a 2- or 4-piperidine ring or a 2-azacycloheptane ring; isolating the product of said reaction; and optionally converting said isolated product into a salt.

11. A process for preparing a compound of formula (I) according to claim 1, wherein $R_3$ and $R_4$, together with the carbon atom to which they are attached, form a 2- or 3-pyrrolidine ring, a 2- or 4-piperidine ring or a 2-azacycloheptane ring in which the nitrogen atom is substituted with a radical —CO—alk—$NR_6R_{12}$ in which $R_6$ and $R_{12}$ each represent a hydrogen atom, said process comprising reacting a compound of formula (I) for which $R_3$ and $R_4$, together with the carbon atom to which they are attached, form a 2- or 3-pyrrolidine ring, a 2- or 4-piperidine ring or a 2-azacycloheptane ring, with a derivative of formula (XII):

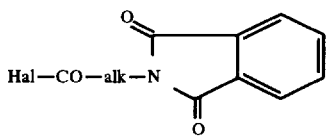

(XII)

in which Hal represents a halogen atom and alk represents an alkyl radical; deprotecting the $NH_2$ thereof; isolating the product of said deprotection; and optionally converting said isolated product into a salt.

39

12. A process for preparing a compound of formula (I) according to claim 1, wherein $R_3$ and $R_4$, together with the carbon atom to which they are attached, form a 2- or 3-pyrrolidine ring, a 2- or 4-piperidine ring or a 2-azacycloheptane ring in which the nitrogen atom is substituted with an alkyl radical having 2 to 6 carbon atoms, a —COOR$_{11}$, —alk—Het, —alk—NR$_6$R$_8$, —alk—COOR$_6$, —alk—Ar", —CO—alk, —CO—alk—COOR$_6$, —CO—alk—NR$_6$R$_{12}$ or —CO—COOR$_6$ radical, or a radical —CO-cycloalkyl in which the cycloalkyl is optionally substituted in the 2-position with a carboxyl, —CO—Ar", —CO—alk—Ar", —CO—Het, —CO—alk—Het, —CO—N(alk)alk', —SO$_2$—alk or —SO$_2$—Ar radical, said process comprising reacting a compound of formula (I) for which $R_3$ and $R_4$, together with the carbon atom to which they are attached, form a 2- or 3-pyrrolidine ring, a 2- or 4-piperidine ring or a 2-azacycloheptane ring, with a halide Hal—Rc in which Hal represents a halogen and Rc represents an alkyl radical having 2 to 6 carbon atoms, —COOR$_{11}$, —alk—Het, —alk—NR$_6$R$_8$, —alk—COOR$_6$, —alk—Ar", —CO—alk, —CO—alk—COOR$_6$, —CO—alk—NR$_6$R$_{12}$ or —CO—COOR$_6$ radical or a radical —CO-cycloalkyl containing 3 to 6 carbon atoms in which the cycloalkyl is optionally substituted in the 2-position with a carboxyl, —CO—Ar", —CO—alk—Ar", —CO—Het, —CO—alk—Het, —CO—N(alk)alk', —SO$_2$—alk or —SO$_2$—Ar radical, alk, alk', Het, $R_6$, $R_8$, $R_{11}$, $R_{12}$, Ar and Ar" having the same meanings as recited in claim 1; isolating the product of said reaction; and optionally converting said isolated product into a salt.

13. A process for preparing a compound of formula (I) according to claim 1, wherein $R_3$ and $R_4$, together with the carbon atom to which they are attached, form a 2- or 3-pyrrolidine ring, a 2- or 4-piperidine ring or a 2-azacycloheptane ring in which the nitrogen atom is substituted with a radical —CO—alk—CONR$_6$R$_8$ or —alk—CO—NR$_6$R$_8$, said process comprising reacting a compound of formula (I) in which $R_3$ and $R_4$, together with the carbon atom to which they are attached, form a 2- or 3-pyrrolidine ring, a 2- or 4-piperidine ring or a 2-azacycloheptane ring in which the nitrogen atom is substituted with a radical —CO—alk—COOR$_6$ or —alk—COOR$_6$, with an amine HNR$_6$R$_8$ in which $R_6$ and $R_8$ have the same meanings as recited in claim 1; isolating the product of said reaction; and optionally converting said isolated product into a salt.

14. A process for preparing a compound of formula (I) according to claim 1, wherein $R_3$ and $R_4$, together with the carbon atom to which they are attached, form a 2- or 3-pyrrolidine ring, a 2- or 4-piperidine ring or a 2-azacycloheptane ring in which the nitrogen atom is substituted with a —CHO radical, said process comprising reacting a compound of formula (I) in which $R_3$ and $R_4$, together with the carbon atom to which they are attached, form a 2- or 3-pyrrolidine ring, a 2- or 4-piperidine ring or a 2-azacycloheptane ring, with CH$_3$COOCHO; isolating the product of said reaction; and optionally converting said isolated product into a salt.

15. A process for preparing a compound of formula (I) according to claim 1, wherein $R_3$ and $R_4$, together with the carbon atom to which they are attached, form a 2- or 3-pyrrolidine ring, a 2- or 4-piperidine ring or a 2-azacycloheptane ring in which the nitrogen atom is substituted with a radical —CO—Het, —CO—alk—COOR$_6$, —CO—COOR$_6$, —CO—alk—NR$_6$R$_{12}$, —CO—Ar", —CO—alk—Ar", —CO—alk—Het or —CO—alk or a radical —CO-cycloalkyl in which the cycloalkyl is optionally substituted in the 2-position with a carboxyl radical, said process comprising reacting a compound of formula (I) in which $R_3$ and $R_4$, together with the carbon atom to which they are attached, form a 2- or 3-pyrrolidine ring, a 2- or 4-piperidine ring or a 2-azacycloheptane ring, with a derivative HO—Rd in which Rd represents a radical —CO—Het, —CO—alk—COOR$_6$, —CO—COOR$_6$, —CO—alk—NR$_6$R$_{12}$, —CO—Ar", —CO—alk—Ar", —CO—alk—Het or —CO—alk, or a radical —CO-cycloalkyl containing 3 to 6 carbon atoms in which the cycloalkyl is optionally substituted in the 2-position with a carboxyl radical, Het, alk, $R_6$, $R_8$, $R_{12}$, Het and Ar" having the same meanings as recited in claim 1; isolating the product of said reaction; and optionally converting said isolated product into a salt.

16. A process for preparing a compound of formula (I) according to claim 1, wherein $R_3$ and $R_4$, together with the carbon atom to which they are attached, form a 2- or 3-pyrrolidine ring, a 2- or 4-piperidine ring or a 2-azacycloheptane ring in which the nitrogen atom is substituted with a radical —CO—alk—COOR$_6$ in which alk contains 1 to 3 carbon atoms in a straight chain, a radical —CO—CH$_2$—C(CH$_3$)$_2$—CH$_2$—COOR$_6$, —CO—CH$_2$—CH$_2$—C(CH$_3$)$_2$—COOR$_6$, —CO—CH$_2$—C(CH$_3$)$_2$—COOR$_6$, —CO—CH$_2$—O—CH$_2$—COOR$_6$, —CO—CH$_2$—S—CH$_2$—COOR$_6$ or —CO—CH=CH—COOR$_6$, a radical —CO-cycloalkyl (6C) in which the cycloalkyl is substituted in the 2-position with a carboxyl radical, a radical —CO—Ar" in which Ar" represents a phenyl radical substituted in the 2-position with a carboxyl radical, or a radical —CO—Het in which Het represents a 2- or 4-pyridyl radical substituted in the 3-position with a carboxyl radical or a 3-pyridyl radical substituted in the 4-position with a carboxyl radical and $R_6$ represents a hydrogen atom, said process comprising reacting an anhydride of formulae:

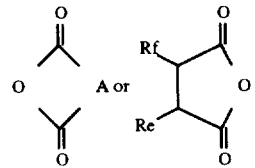

in which A represents an alkyl radical having 1 to 3 carbon atoms in a straight chain, —CH$_2$—C(CH$_3$)$_2$—CH$_2$—, —CH$_2$—CH$_2$—C(CH$_3$)$_2$—, —CH$_2$—C(CH$_3$)$_2$—, —CH$_2$—O—CH$_2$—, —CH$_2$—S—CH$_2$ or —CH=CH—, Re and Rf form, together with the 2 carbon atoms to which they are attached, a cycloalkyl(6C), phenyl or pyridyl radical, with a compound of formula (I) for which $R_3$ and $R_4$, together with the carbon atom to which they are attached, form a 2- or 3-pyrrolidine ring, a 2- or 4-piperidine ring or a 2-azacycloheptane ring; isolating the product of said reaction; and optionally converting said isolated product into a salt.

17. A process for preparing the compound of formula (I) according to claim 1, wherein $R_3$ and $R_4$, together with the carbon atom to which they are attached, form a 2- or 3-pyrrolidine ring, a 2- or 4-piperidine ring or a 2-azacycloheptane ring in which the nitrogen atom is substituted with a radical —CO—NH—alk—Ar", —CO—NH—Het, —CO—NH—alk—Het, —CO—NH—Ar", —CO—NH—alk, —CO—NH$_2$, —CSNH$_2$, —CS—NH—alk, —CS—NH—Ar" or —CS—NH—Het, said process comprising reacting a compound of formula (I) for which $R_3$ and $R_4$, together with the carbon atom to which they are attached, form a 2- or 3-pyrrolidine ring, a 2- or 4-piperidine ring or a 2-azacycloheptane ring with a derivative of formula Rg=C=N—Rh in which Rg represents an oxygen or sulphur atom and Rh represents a trimethylsilyl, alkyl, Het, —alk—Ar", —alk—Het or Ar" radical, Het, alk and Ar" having the same meanings as recited in claim 1; isolating the product of said reaction; and optionally converting said isolated product into a salt.

18. A process for preparing a compound of formula (I) according to claim 1, wherein $R_3$ and $R_4$, together with the carbon atom to which they are attached, form a 2- or 3-pyrrolidine ring, a 2- or 4-piperidine ring or a 2-azacycloheptane ring in which the nitrogen atom is substituted with a radical —CO—alk—$NR_6$—$R_{12}$ in which $R_6$ represents a hydrogen atom and $R_{12}$ represents a radical —CO—NH—alk, said process comprising reacting a compound of formula (I) in which $R_3$ and $R_4$, together with the carbon atom to which they are attached, form a 2- or 3-pyrrolidine ring, a 2- or 4-piperidine ring or a 2-azacycloheptane ring in which the nitrogen atom is substituted with a radical —CO—alk—$NR_6$—$R_{12}$ in which alk represents an alkyl radical, $R_6$ and $R_{12}$ each represent a hydrogen atom, with an alkyl isocyanate; isolating the product of said reaction; and optionally converting said isolated product into a salt.

19. A process for preparing a compound of formula (I) according to claim 1, wherein R represents a carboxyl radical, said process comprising hydrolysing a compound of formula (I), in which R represents an alkoxycarbonyl radical; isolating the product of said hydrolysation; and optionally converting said isolated product into a salt.

20. A pharmaceutical composition comprising a pharmaceutically effective amount of at least one compound of formula (I) according to claim 1 or a salt thereof and a pharmaceutically acceptable carrier.

21. A pharmaceutical composition comprising a pharmaceutically effective amount of at least one compound of formula (I) according to claim 2 or a salt thereof and a pharmaceutically acceptable carrier.

22. A method for antagonizing at least one AMPA receptor, said method comprising administering to a host in need of said antagonizing an effective amount of a compound prepared according to claim 17.

23. A method for antagonizing at least one NMDA receptor, said method comprising administering to a host in need of said antagonizing an effective amount of a compound prepared according to claim 18.

* * * * *